US010004467B2

(12) United States Patent
Lahm et al.

(10) Patent No.: US 10,004,467 B2
(45) Date of Patent: Jun. 26, 2018

(54) GUIDANCE SYSTEM FOR LOCALIZATION AND CANNULATION OF THE CORONARY SINUS

(71) Applicant: Medtronic, Inc., Minneapolis, MN (US)

(72) Inventors: Ryan P. Lahm, Lino Lakes, MN (US); Ronald Alan Drake, Saint Louis Park, MN (US); Eric A. Schilling, Ham Lake, MN (US); Brian W. Schousek, Houlton, WI (US); Mark W. Shepler, White Bear Lake, MN (US); Lester O. Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 260 days.

(21) Appl. No.: 14/261,990

(22) Filed: Apr. 25, 2014

(65) Prior Publication Data

US 2015/0305695 A1    Oct. 29, 2015

(51) Int. Cl.
*A61B 6/12* (2006.01)
*A61B 5/06* (2006.01)
(Continued)

(52) U.S. Cl.
CPC ............... *A61B 6/12* (2013.01); *A61B 5/061* (2013.01); *A61B 6/487* (2013.01); *A61B 6/503* (2013.01); *G06F 19/321* (2013.01); *G06T 7/0014* (2013.01); *G06T 7/74* (2017.01); *G16H 50/50* (2018.01); *A61B 5/0215* (2013.01); *A61B 5/7435* (2013.01); *A61B 6/4441* (2013.01); *A61B 6/462* (2013.01); *A61B 6/5211* (2013.01);
(Continued)

(58) Field of Classification Search
CPC ......... A61B 5/061; A61B 5/7435; A61B 6/12; A61B 6/4441; A61B 6/462; A61B 6/487; A61B 6/503; A61B 6/5211; A61B 6/5294; G06F 19/321; G06F 19/3437; G06T 2207/10121; G06T 2207/30101; G06T 7/0012; G06T 7/0014; G06T 7/0044; G06T 7/602
See application file for complete search history.

(56) References Cited

U.S. PATENT DOCUMENTS 4,838,879 A    6/1989  Tanabe et al.
5,638,819 A *  6/1997  Manwaring .......... A61B 1/0005
                                                600/103
(Continued)

FOREIGN PATENT DOCUMENTS

WO    2006137063    12/2006

OTHER PUBLICATIONS (PCT/US2015/022133) PCT Notification of Transmittal of the International Search Report and the Written Opinion of the International Searching Authority, dated Sep. 16, 2015, 14 pages.

*Primary Examiner* — Katherine Fernandez

(57) ABSTRACT

A high contrast instrument, such as a radiopaque portion, can be captured and/or viewed in an image that is acquired with an imaging system, such as with a fluoroscopic imaging system. A statistical model can be used to assist in identifying a possible or probable location of a target. A user may move the instrument coil to the statistically probable location of the target to, for example, perform a procedure or carry out a task.

19 Claims, 15 Drawing Sheets

(51) Int. Cl.
    *G06T 7/00*    (2017.01)
    *G06F 19/00*   (2018.01)
    *G06T 7/73*    (2017.01)
    *G16H 50/50*   (2018.01)
    *A61B 5/00*        (2006.01)
    *A61B 6/00*        (2006.01)
    *A61B 5/0215*      (2006.01)

(52) U.S. Cl.
    CPC ... *A61B 6/5294* (2013.01); *G06T 2207/10121* (2013.01); *G06T 2207/30048* (2013.01); *G06T 2207/30101* (2013.01)

(56) References Cited

U.S. PATENT DOCUMENTS

| | | | |
|---|---|---|---|
| 6,285,903 B1 | 9/2001 | Rosenthal et al. | |
| 6,623,518 B2 | 9/2003 | Thompson et al. | |
| 6,980,675 B2 | 12/2005 | Evron et al. | |
| 7,225,012 B1 * | 5/2007 | Susil | A61B 90/36 600/407 |
| 7,308,299 B2 | 12/2007 | Burrell et al. | |
| 7,321,677 B2 | 1/2008 | Evron et al. | |
| 7,327,872 B2 | 2/2008 | Vaillant et al. | |
| 7,499,743 B2 | 3/2009 | Vass et al. | |
| 7,587,074 B2 | 9/2009 | Zarkh et al. | |
| 7,742,629 B2 | 6/2010 | Zarkh et al. | |
| 7,778,685 B2 | 8/2010 | Evron et al. | |
| 7,778,686 B2 | 8/2010 | Vass et al. | |
| 7,797,030 B2 | 9/2010 | Lahm et al. | |
| 7,813,785 B2 | 10/2010 | Okerlund et al. | |
| 7,996,063 B2 | 8/2011 | Vass et al. | |
| 8,073,213 B2 | 12/2011 | Vaillant et al. | |
| 8,515,527 B2 | 8/2013 | Vaillant et al. | |
| 9,033,996 B1 | 5/2015 | West | |
| 2003/0018251 A1 * | 1/2003 | Solomon | A61B 5/04011 600/427 |
| 2003/0220555 A1 * | 11/2003 | Heigl | A61B 6/12 600/407 |
| 2005/0008210 A1 | 1/2005 | Evron et al. | |
| 2005/0148850 A1 * | 7/2005 | Lahm | A61B 5/06 600/407 |
| 2006/0004286 A1 * | 1/2006 | Chang | A61B 5/06 600/435 |
| 2006/0074285 A1 | 4/2006 | Zarkh et al. | |
| 2011/0112398 A1 | 5/2011 | Zarkh et al. | |
| 2012/0232478 A1 | 9/2012 | Haslinger | |
| 2013/0116739 A1 | 5/2013 | Brada et al. | |
| 2014/0058251 A1 * | 2/2014 | Stigall | A61B 5/1076 600/424 |
| 2014/0187921 A1 * | 7/2014 | Nakada | A61B 6/12 600/424 |

* cited by examiner

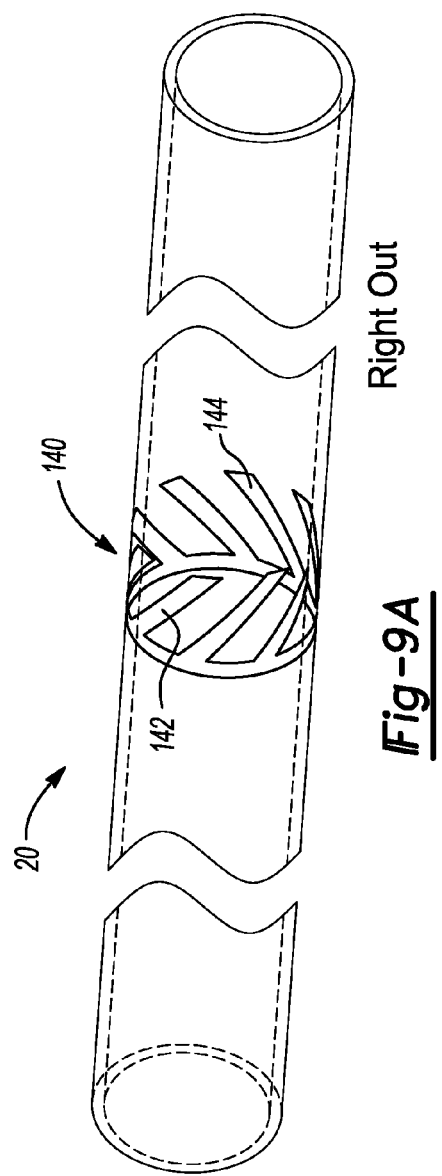
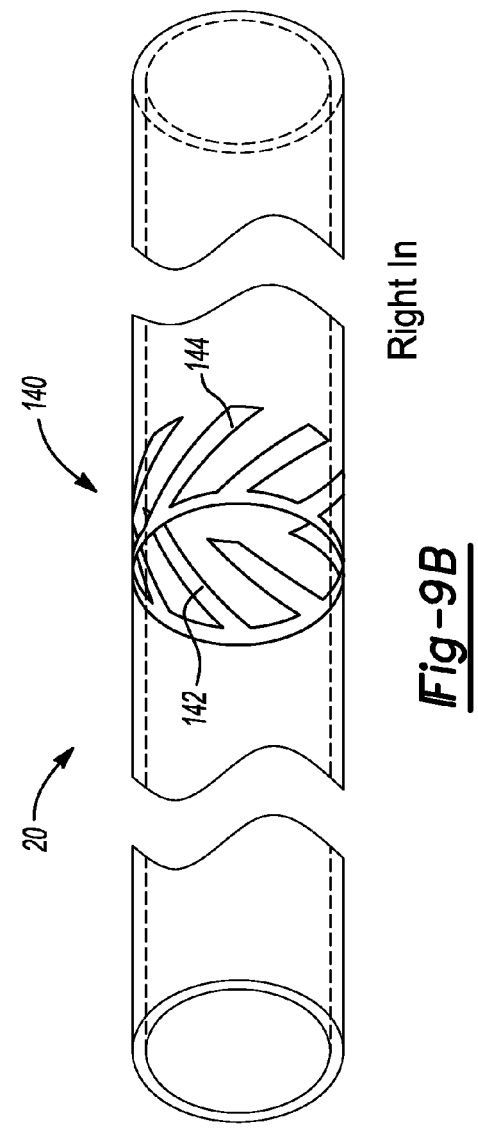

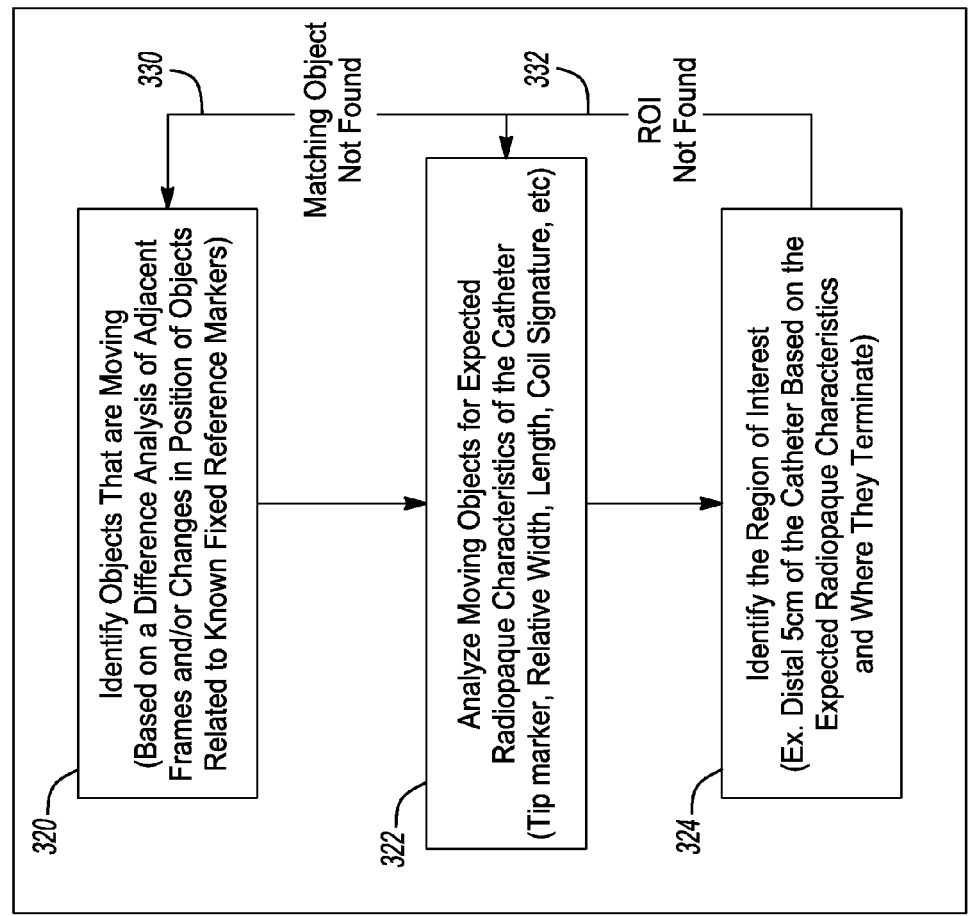
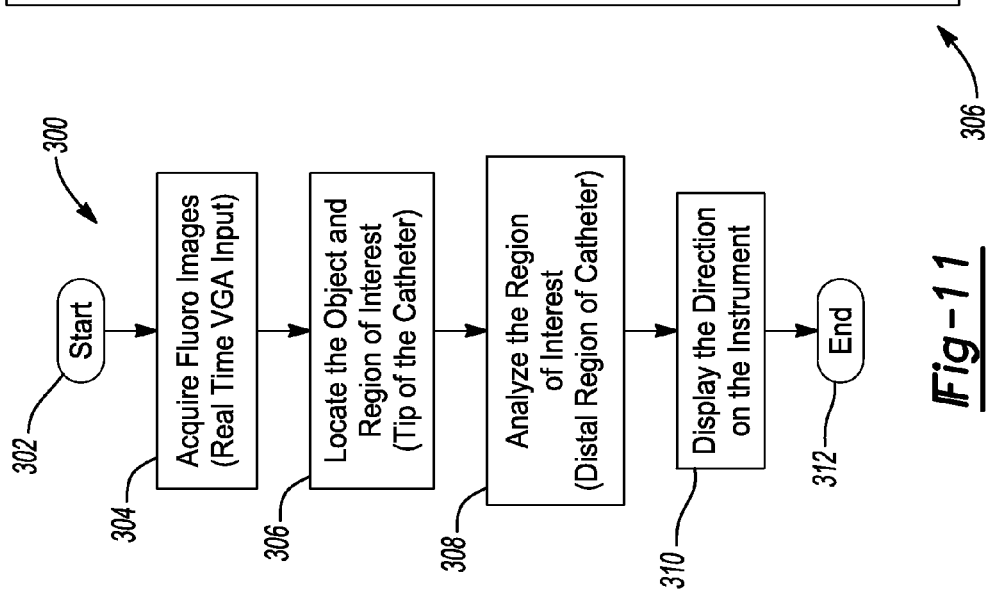

GUIDANCE SYSTEM FOR LOCALIZATION AND CANNULATION OF THE CORONARY SINUS

FIELD

The subject disclosure is related generally to a system for assisting in a surgical procedure, in particular to assisting in determining a location and orientation of a portion of an anatomy and an instrument relative thereto.

BACKGROUND

During various surgical procedures, such as the positioning of a lead in or near a heart of a patient, a position for a lead can be selected by a surgeon, electrophysiologist, or other appropriate user. The position of the lead may be at a target location, such as in a coronary sinus of a human subject or at a branch of the coronary sinus in the heart. The positioning of the lead can include a wedging or interference fit, a passive non-interference fit, or an active fixation of a lead into a coronary vessel of a patient.

Various leads can include the Attain™ cardiac leads sold by Medtronic, Inc. The leads can include various shapes and configurations to be positioned into the coronary vessels or other selected locations of the patient. The leads can provide stimulation, such as with an implanted cardiac resynchronization system, including a pacemaker or defibrillator. The lead can be positioned within the patient to provide stimulation to an appropriate portion of the anatomy, such as a selected portion of the heart, to stimulate a dyssynchronous region of the heart. Generally, the lead can be positioned to stimulate a late activating portion of the heart.

A venogram can be obtained of the patient by a user. The venogram of the patient can be used to identify selected locations for stimulation of the heart. Generally, a venogram can include a contrast-enhanced image of a portion of the patient, such as a vein structure of a patient. A contrast-enhanced image, however, generally requires the positioning of a contrast agent in a venous structure which, also, requires positioning of a catheter or delivery device for a contrast agent at the vein structure.

SUMMARY

This section provides a general summary of the disclosure, and is not a comprehensive disclosure of its full scope or all of its features.

Positioning of an appropriate lead within the patient can be based upon image data acquired of the patient and user input and experience. Generally, the positioning of a lead within the coronary vessels may need to account for the geometry of the vessels, tortuosity of a path through vessels to reach a target location, and/or diameter of the coronary vessels. The appropriate lead to be positioned within the coronary vessels, or other appropriate positions for stimulation in a patient, may be selected based upon various factors, including a diameter of the lead, other physical factors of the lead, and user experience.

Using various systems, such as the CardioGuide™ implant system sold by Medtronic, Inc., image data can be acquired of a patient to identify various portions of the anatomy. For example, image data acquired during venograms can be assimilated or reconstructed into a three-dimensional model of the coronary vasculature of a subject, such as a human patient. The three-dimensional image of the coronary vasculature can include geometric, size, and configuration information regarding various portions of the anatomy, tortuosity of a path to reach a target location, vessel size to reach a coronary vessel, size of the vessel, location of the vessel, etc. In addition to the geometric shape and configuration of the patient, image data can incorporate or include physiological data, such as contraction timing, motion change, and the like. For example, image data can be acquired at a single time to generate a static three-dimensional model. Image data may also be acquired over time, such as about 30 frames per second, to acquire contraction timing data regarding a patient.

A system that can generate images of a patient, such as a vascular system of a patient, using fluoroscopic images may require the injection of a contrast agent into the vasculature of a patient. To inject a contrast agent into a vasculature of a heart of a patient, access to a coronary sinus ostium (herein CSOs) is generally obtained. According to various embodiments a catheter can be positioned in or near the CSOs and a contrast agent can be injected to allow a contrast agent to flow through a vasculature around a heart. Images can be acquired of the patient, such as with a fluoroscopic system, during the flow time of the contrast agent.

Prior to the injection of a contrast agent into a patient's vascular system, however, fluoroscopic images (generally using x-rays) do not provide high contrast view of non-radiopaque portions. For example, non-radiopaque portions can include soft tissues of the heart. A high contrast instrument, such as a radiopaque portion of a catheter, can be viewed with a fluoroscopic imaging system. Further, a statistical model or model of a statistically "average subject" can be used to assist in identifying a possible or statistically probable location of the CSOs. A user, such as a surgeon, can then move the catheter towards a statistically probable location and orientation of the CSOs to assist in cannulating the CSOs and allowing injection of a contrast agent into the CSOs for flowing through the vascular system of the patient. As discussed herein, various techniques can be used to assist in cannulating the CSOs, such as real time tracking (i.e. viewing) of the relative position of an instrument and the predicted CSOs location, measurement of the instrument location and direction based on radiopaque landmarks and views of the instrument, etc.

Further areas of applicability will become apparent from the description provided herein. The description and specific examples in this summary are intended for purposes of illustration only and are not intended to limit the scope of the present disclosure.

DRAWINGS

Example embodiments will now be described more fully with reference to the accompanying drawings.

Figure 8A:
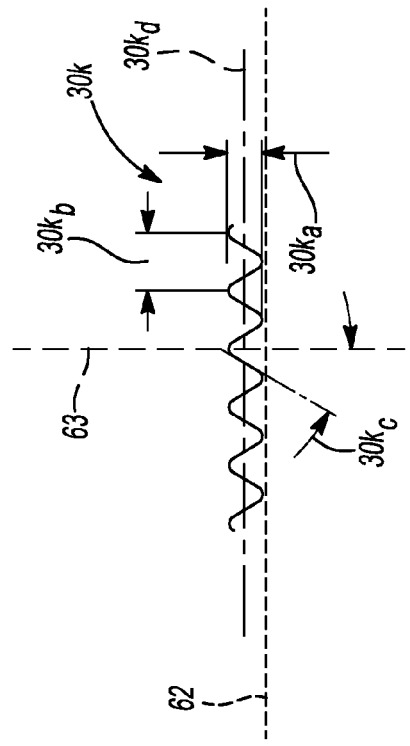
FIG. 8A is a schematic representation of an imageable portion with a first pitch and diameter and its orientation relative to a plane.
Figure 8A:
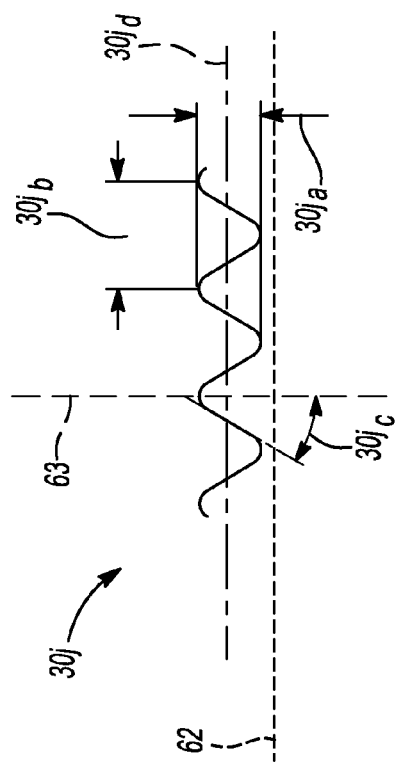
Figure 8B:
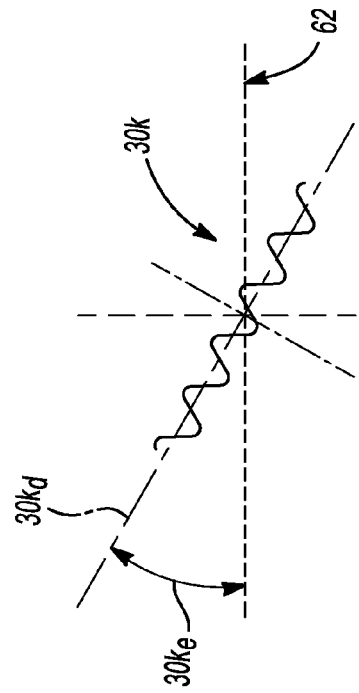
Figure 8B:
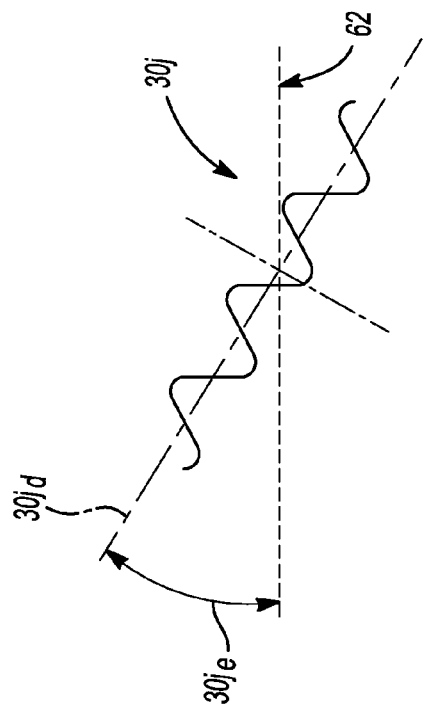
Figure 10:
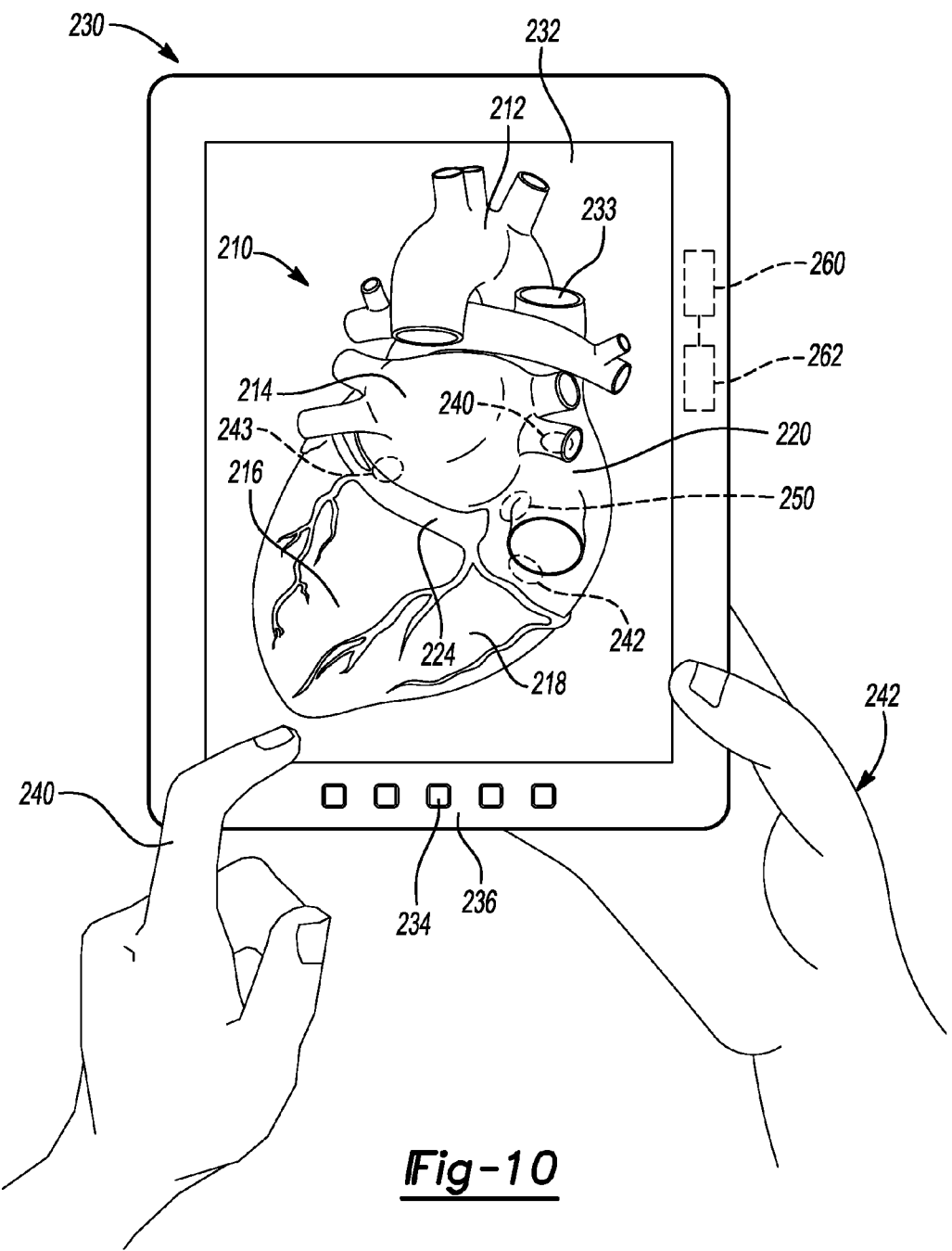
Figure 13:
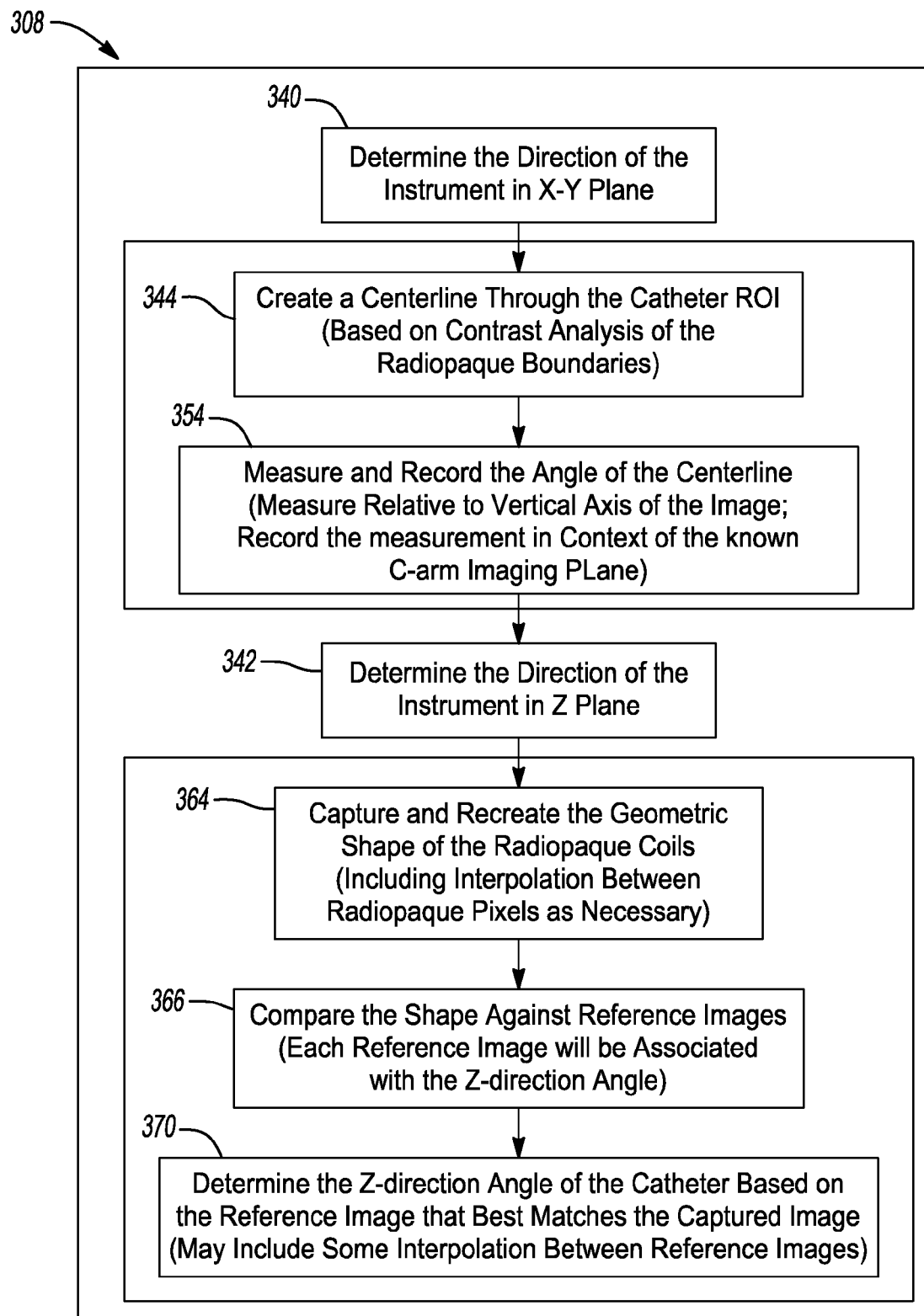
Figure 14:
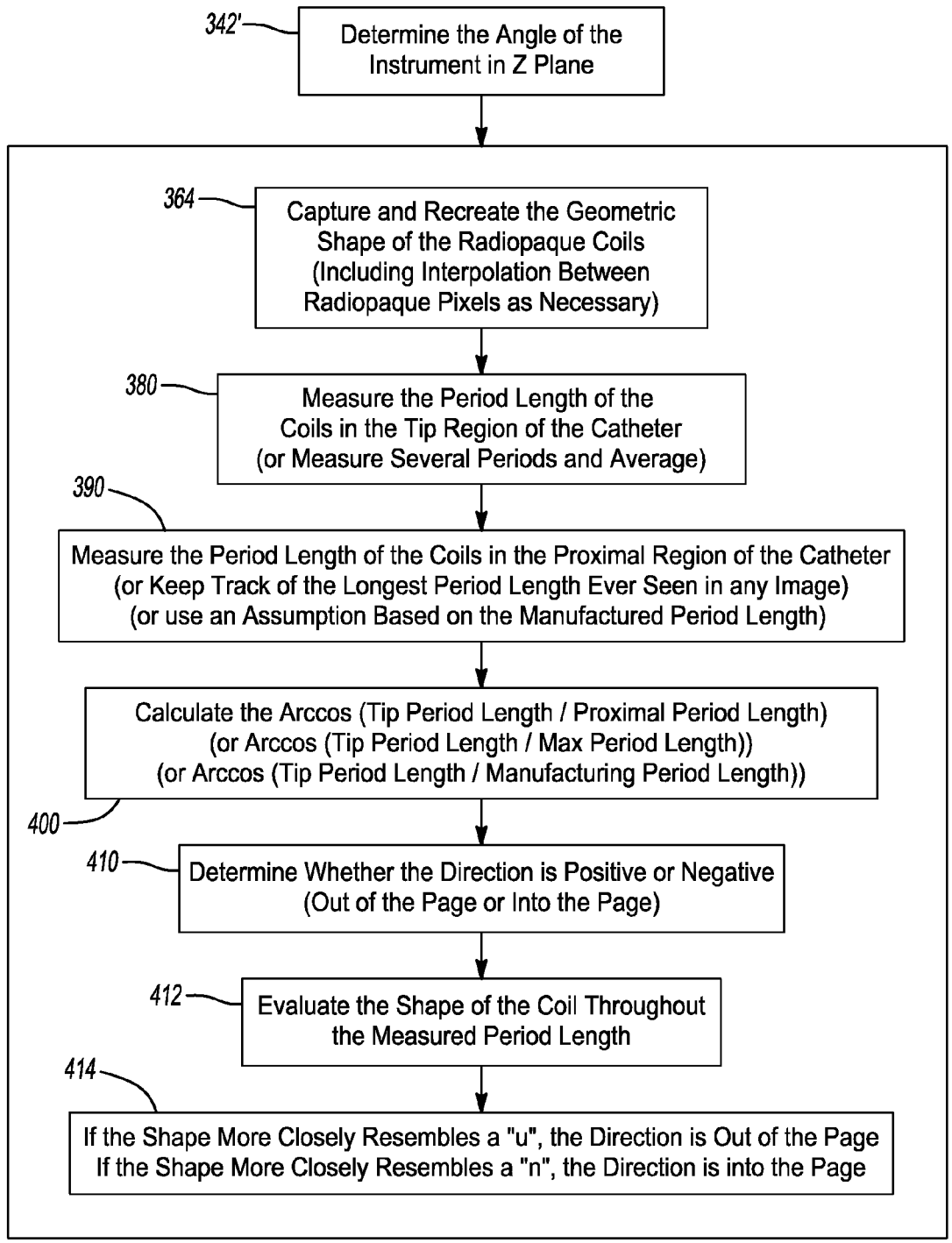
Figure 15:
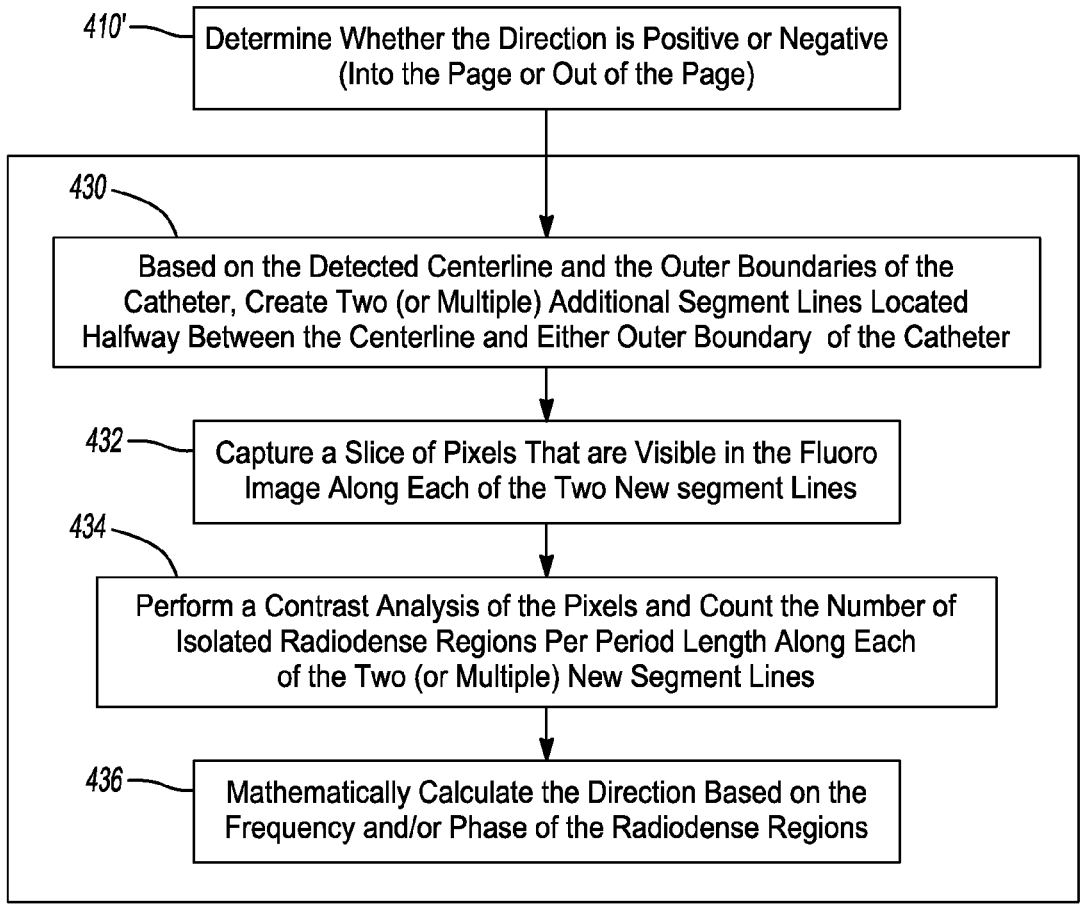
Figure 16:
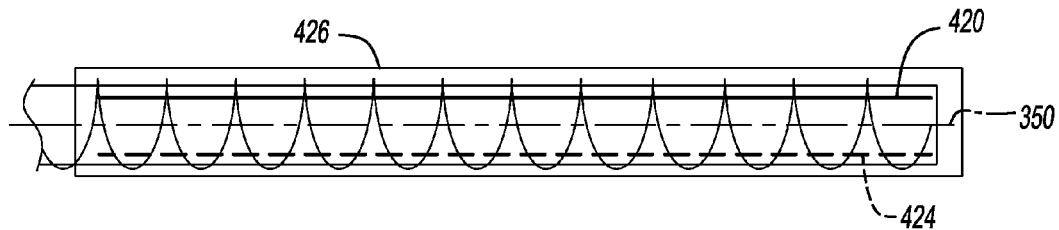
Figure 17:
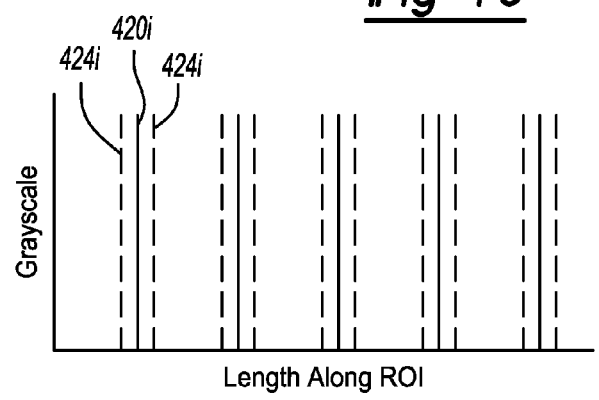
Figure 18:
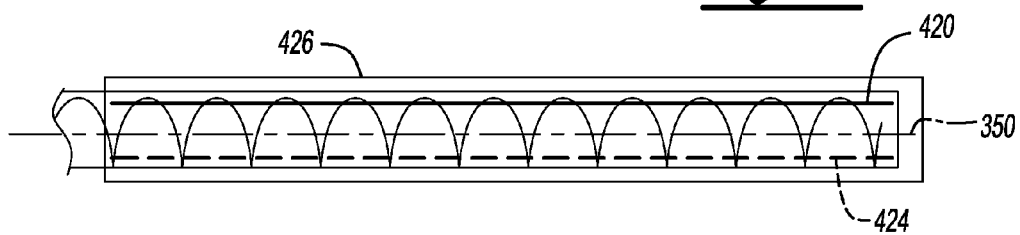
Figure 19:
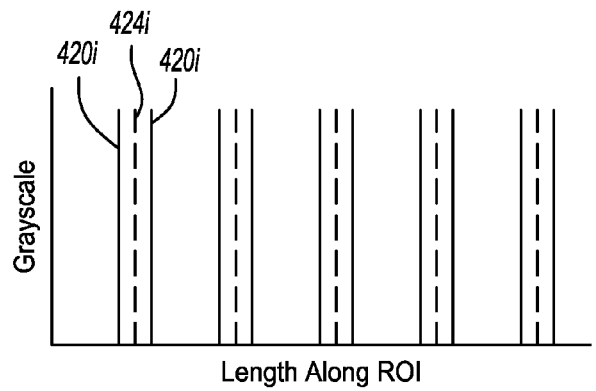
Figure 20:
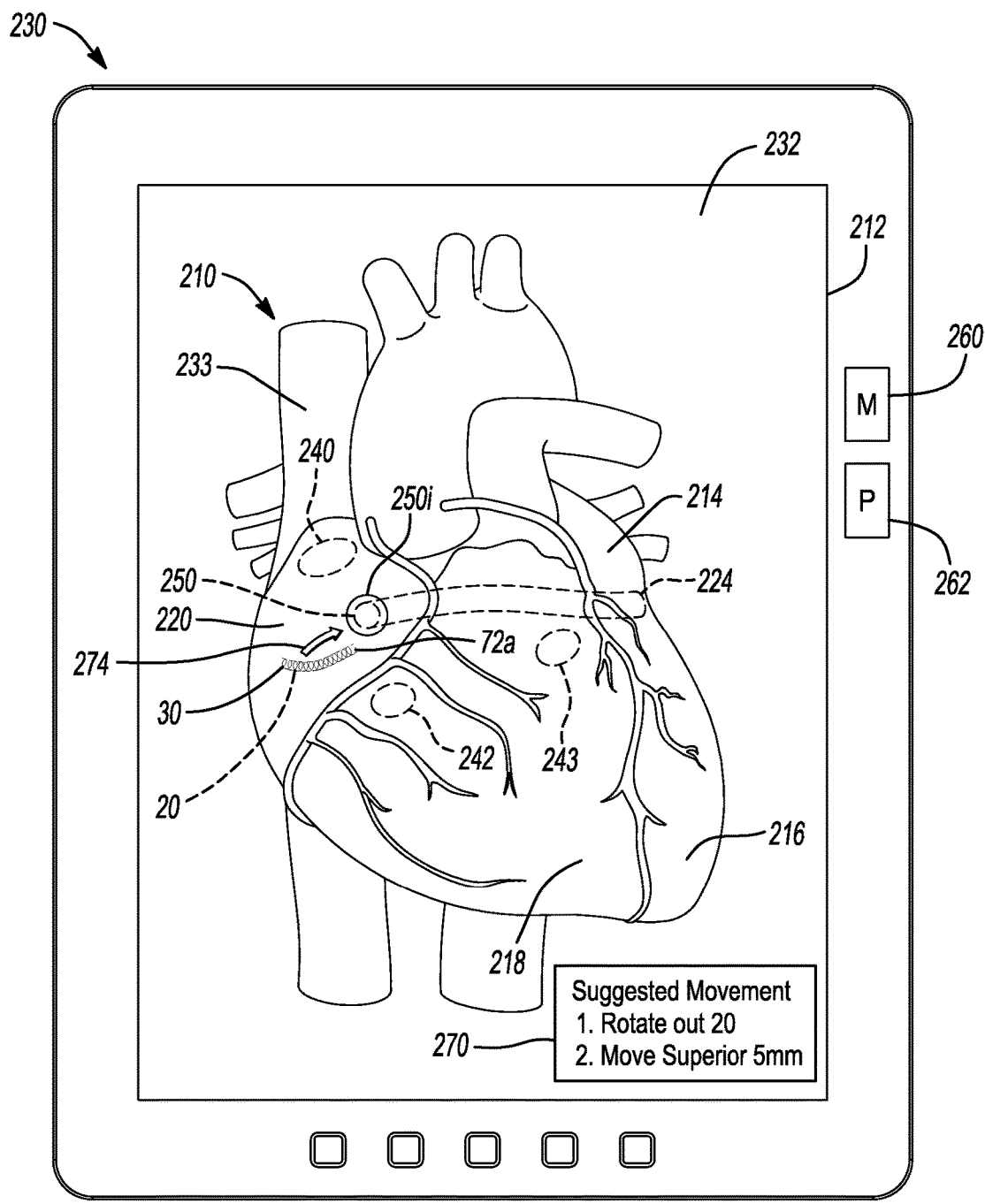
Figure 21:
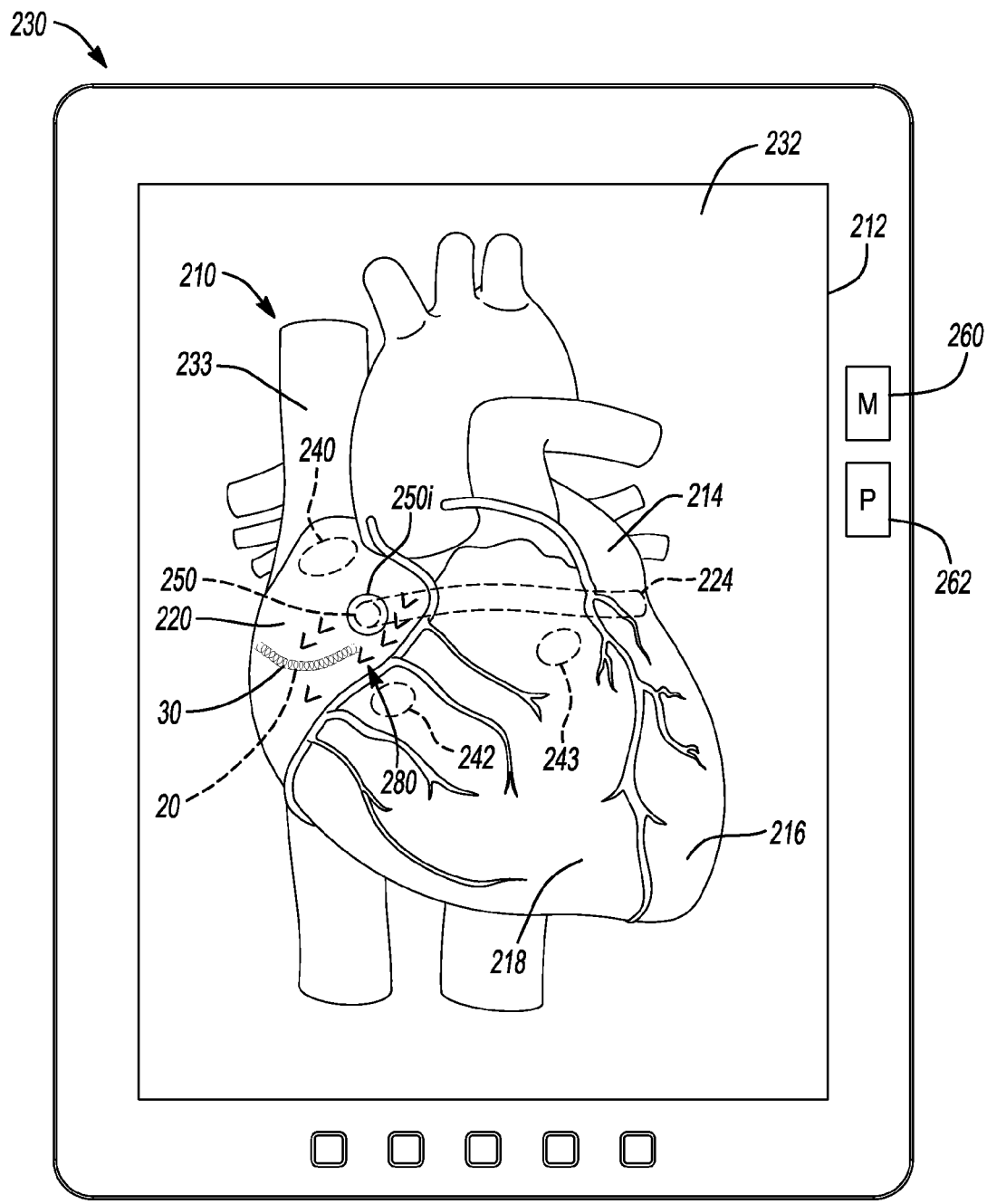

FIG. 8Aa is a schematic representation of an imageable portion with the first pitch and diameter and its orientation relative to the plane;

FIG. 8B is a schematic representation of an imageable portion with a second pitch and diameter and its orientation relative to a plane;

FIG. 8Bb is a schematic representation of an imageable portion with the second pitch and diameter and its orientation relative to the plane;

FIG. 9A is a screen shot of a display illustrating a configuration of an imageable portion for determining an angle of the imageable portion;

FIG. 9B is a screen shot of a display illustrating a configuration of an imageable portion for determining an angle of the imageable portion;

FIG. 10 is an environmental view of a display and/or computing and processing device, operable to display image data and/or the screenshots;

FIG. 11 is a flowchart illustrating a method of determining an angle of an imageable portion;

FIG. 12 is a flowchart illustrating, in detail, at least a sub-routine, according to various embodiments, of the method illustrated in FIG. 11;

FIG. 13 is a flowchart illustrating, in detail, at least a sub-routine, according to various embodiments, of the method illustrated in FIG. 11;

FIG. 14 is a flowchart illustrating, in detail, at least a sub-routine, according to various embodiments, of the method illustrated in FIG. 11;

FIG. 15 is a flowchart illustrating, in detail, at least a sub-routine, according to various embodiments, of the method illustrated in FIG. 11;

FIG. 16 is a schematic illustration of a representation of the method illustrated in FIG. 15, according to various embodiments;

FIG. 17 is a graph illustrating the results of the analysis of FIG. 16, according to various embodiments;

FIG. 18 is a schematic illustration of a representation of the method illustrated in FIG. 15, according to various embodiments;

FIG. 19 is a graph illustrating the results of the analysis of FIG. 18, according to various embodiments;

FIG. 20 is an environmental view of a display and/or computing and processing device, operable to display image data and/or the screenshots, according to various embodiments; and FIG. 21 is an environmental view of a display and/or computing and processing device, operable to display image data and/or the screenshots, according to various embodiments.

Corresponding reference numerals indicate corresponding parts throughout the several views of the drawings.

DETAILED DESCRIPTION

Example embodiments will now be described more fully with reference to the accompanying drawings.

A system can be used to acquire image data of a patient and reconstruction a three-dimensional view of at least a portion of a subject or device. For example, image data can be acquired of a patient's heart and vessel structure and a three-dimensional reconstruction of the patient's heart and vessel structure can be made. Various systems to generate such a three-dimensional reconstruction with acquired image data include the CardioGuide™ sold by Medtronic, Inc. Additionally, various systems include those disclosed in U.S. Pat. Nos. 7,778,685; 7,742,629; 7,587,074; 7,321,677; and 6,980,675; and U.S. Pat. App. Pub. No. 2013/0116739, 2011/0112398, 2006/0074285, and 2005/0008210, all incorporated herein by reference. Generally, the patient imaging systems can acquire image data of a patient using various techniques, such as a venogram. In venogram procedures, a contrast agent is injected into a patient and x-ray images are acquired of the patient, such as a patient's coronary sinus, while the contrast agent is in and traveling through a vessel in a vasculature of the patient. Accordingly, one or more images of the patient is acquired with the contrast agent flowing through the patient's vessels to allow imaging of the vessels of the patient. The imaging generates image data that allows image reconstruction to be made of the patient, such as a three-dimensional (3D) reconstruction, based upon the image data that can include two or more x-ray projections. The x-ray projections may be two-dimensional projections that are used to form a reconstruction. It is also understood that a plurality of projections can be acquired of the patient over time to allow for a motion reconstruction of the patient, including motion of the coronary sinus during a heart cycle. In various embodiments, the image data can be used to reconstruct a three-dimensional model of portions of the patient, such as the patient's heart, patient's vasculature system, and the like.

It is understood, however, that various other members can be imaged and reconstructed. For example, inanimate objects, including complex machinery, robotics, hydraulic systems, and the like can also be imaged or analyzed. In various embodiments, computer-aided design images can be used to assist in determining the geometry, size, and the like of various portions of machinery. Accordingly, although the following description is related generally to an imaging, planning, and/or guiding procedure relative to a human subject, the currently disclosed system and/or method can be used with any appropriate non-human system.

In various embodiments, the image data of a subject, such as a human patient or other appropriate non-human patient, can be analyzed. The analysis of the image data can be used for various reasons, such as those discussed further herein. For example, the image data can be analyzed to determine a geometry of a patient's anatomy, a size of various portions of the patient, a pathway or tortuosity of a pathway from a start point (such as an entry point) to a selected target location of the patient, and other appropriate analyses. The tortuosity of a pathway can include the number of curves or turns of the path and a size or angle of the curves. The path can be from an insertion or start point to a target location, as discussed herein. Also, the analyzed shape of the radiopaque or imaged portion can be used to determine an orientation of the instrument, as discussed herein.

Figure 1A:
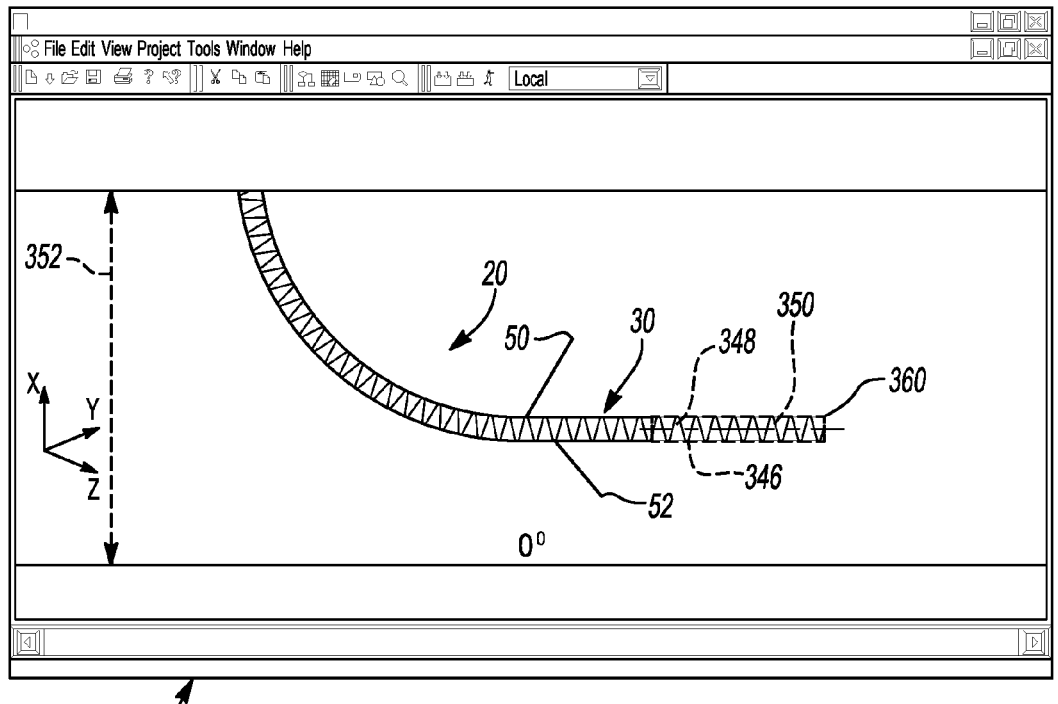
FIG. 1A is a screen shot of a display illustrating a configuration of an imageable portion for determining an angle of the imageable portion.
Figure 1B:
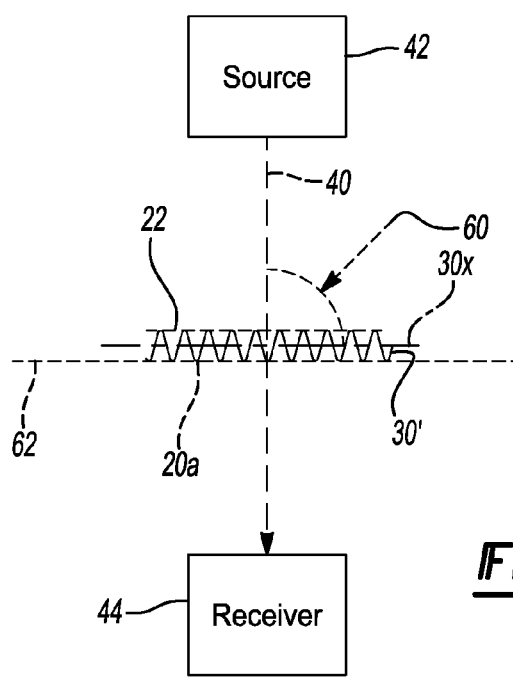
FIG. 1B is a schematic representation of an imaging system to generate the view of the imageable portion and its orientation relative to the imageable portion.

With initial reference to FIGS. 1A and 1B, an instrument 20a, such as a catheter, can be shown in an image 20, such as on a screen or display 21, and can include a catheter or other appropriate instrument that can be placed within a subject, such as a human patient. The catheter 20a can include an exterior wall 22 that can be formed of a selected material, such as a polymer, fabric, or other selected material. Generally the wall 22 is substantially not radiopaque, and, therefore, generally is not shown in high contrast and/or is substantially not viewable on the display 21. Catheters can include the Attain Command™ and/or the Attain Select® II catheter families, sold by Medtronic, Inc., having a place of business in Minnesota. The catheter 20a can include an internal cannula defined by the wall 22 for delivering the material, such as a contrast agent. It is understood, however, that the instrument 20a can also be a solid instrument, such as a solid guide wire or substantially solid guide wire.

The outer wall 22 of the instrument 20a may generally be radio transparent such that a fluoroscopic or other x-ray imaging modality would not generate a high contrast image of the instrument 20a. Accordingly, a radiopaque material, such as a radiopaque wire or thread 30', can be provided with and or formed with the instrument 20a. In various embodiments, the portion 30' may be formed in the wall 22 or in contact with the wall 22. The radiopaque portion 30' can be formed of an appropriate radiopaque material such as a metal (e.g., stainless steel, tungsten, gold, platinum iridium, or other appropriate biocompatible materials), radiopaque polymer fibers, radiopaque fill fibers, polymers with radiopaque additives, or the like. The radiopaque thread portion 30' can be formed into the wall 22 or positioned within the instrument 20a in an appropriate manner, such as during the manufacturing process. The radiopaque portion 30' can be a portion that is high contrast in an x-ray image of the instrument 20.

The radiopaque wire or thread 30 can be formed into the instruments 20 in a selected configuration, such as in a generally helical configuration. For example, the radiopaque thread 30 can be formed in a helical manner and formed into the wall 22 of the instrument 20 in the helical manner. For reference, a thread of a screw or a coiled spring can generally define a helical configuration that can define a template for forming the helical shape of the radiopaque thread 30 in the instrument 20.

A x-ray path 40 is perpendicular to a center plane 62 between a source 42 and a receiver 44 system. The x-ray is like a flashlight that is casting a shadow on the receiver 44. In various embodiments, due to a shape of the radiopaque portion 30' when viewed at a 0° angle relative to the plane 62, the image of the helical radiopaque portion 30 (based upon the physical radiopaque helical portion 30' as illustrated in FIG. 1B), will appear to be substantially sinusoidal and have an even space between each peak 50 and valley 52, as shown in FIG. 1A. It is understood that a length of the radiopaque portion 30' will have a plurality of the peaks 50 and a plurality of the valleys 52 that can be substantially evenly spaced apart along the length of the radiopaque portion 30'. Discussed herein, various processes and techniques can be used to determine the angle of the radiopaque image portion.

Further, as illustrated in FIG. 1A, the image of the radiopaque portion 30 will have a curve at the peak 50 and a curve at the valley 52 that are substantially similar.

Accordingly, a user or a processor system, as discussed further herein, can determine that an axis 30x of the radiopaque portion 30' is at an angle 60 that in this case is substantially perpendicular or at a 90° angle to the ray 40 of the x-rays from the source 42 to the receiver 44. In other words, when the angle 60 is generally at about 90° relative to the ray 40 of the x-rays, the axis 30x of the radiopaque member 30' is substantially parallel, or 0°, with the center plane 62 of the source 42 and the receiver 44 system. It is understood, that a certain error may be present due to the resolution of the imaging system, the display device, or other features. Generally, the determined angle can be about 0.1% to about 10%, including about 1% to about 5% accurate, based on the image of the radiopaque portion. The processor can be any appropriate type of processor operable or configured to execute instructions or designed to perform selected functions. For example, special or application specific purpose processors (ASIC) may be designed and used to perform the processes discussed herein. Also, or in the alternative, a general purpose or central processing unit (CPU) can be programmed to make the determination, such as executing a program including the methods discussed herein. The processors can include integrated circuitry.

As is generally understood by one skilled in the art, the x-rays from the source 42 impact a plate or imaging portion of the receiver 44 which is generally substantially planar. Accordingly, the plane 62 can be substantially parallel with the axis 30x of the radiopaque member 30' to allow for generation of the image illustrated in FIG. 1A and labeled 0°. Accordingly, the axis 30x of the radiopaque member 30' is at 0° relative to the plane 62.

As is understood in the art, to position the instrument 20, such as a catheter, within a subject, such as within the heart of a subject, the instrument may need to be moved from a first position to a second position. Further, a catheter can include a shape, such as having a distal tip that forms an angle relative to a proximal region of the catheter. Accordingly, an orientation of the catheter relative to the patient and/or imaging system, including plane 62, can be determined. The orientation or position of the instrument 20 may be determined to assist in identifying a location of the catheter or instrument 20 relative to the patient and ensuring efficient movement or positioning of the instrument 20 relative to a selected location of the patient, such as a coronary sinus ostium (herein "CSOs"). As discussed further herein, at least one procedure that may be performed on a patient may be cannulation of a CSOs. In a cannulation of the CSOs, an instrument, such as the instrument 20a that can include a catheter, can be positioned within the CSOs and moved at least a distance into the coronary sinus. Generally, the instrument 20 can be moved through a superior vena cava into the right atrium of a heart and then into the CSOs. Although entry into the right atrium may be relatively easy due to the direct access of the right atrium from the superior vena cava, the CSOs may only be formed as a small portion through a wall of the right atrium. Thus, moving the instrument 20 into the CSOs may be more efficiently performed if it is possible to easily identify an orientation of the instrument 20 and/or a location/orientation of the CSOs relative to a current position of the instrument 20.

Figure 2A:
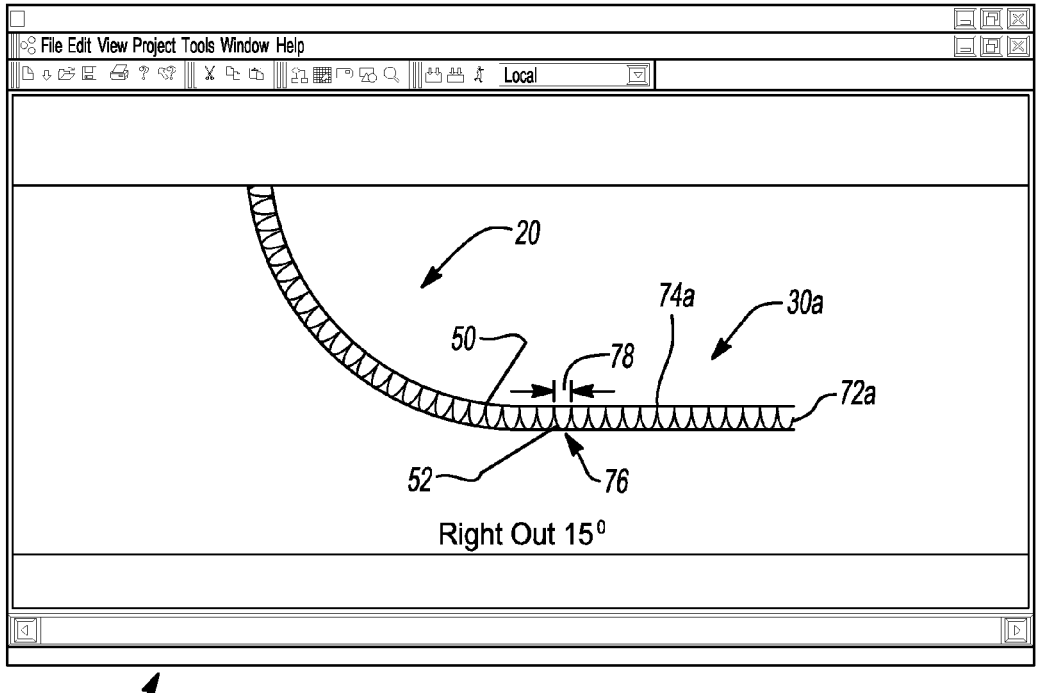
FIG. 2A is a screen shot of a display illustrating a configuration of an imageable portion for determining an angle of the imageable portion.
Figure 2B:
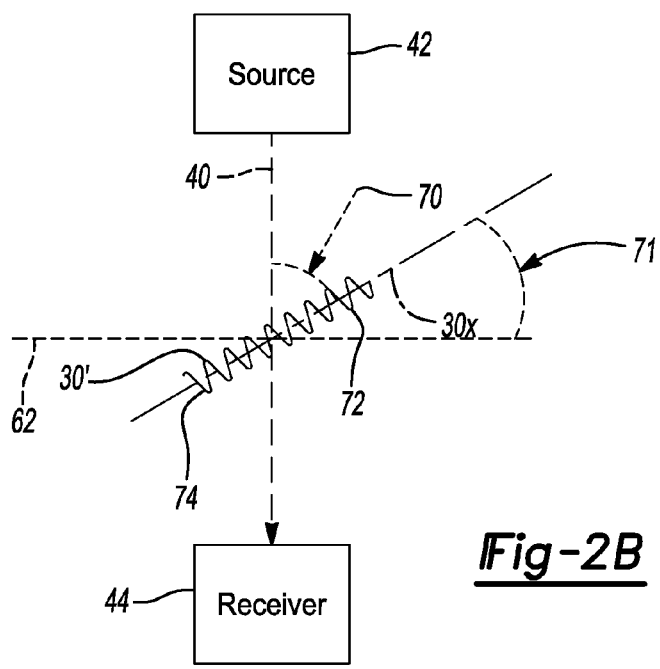
FIG. 2B is a schematic representation of an imaging system to generate the view of the imageable portion and its orientation relative to the imageable portion.

With reference to FIGS. 2A and 2B, the instrument 20 may be moved relative to the plane 62 and relative to a patient, such as a patient's heart. In one example, an image of the radiopaque portion 30' (as illustrated in FIG. 1B) can be illustrated as 30a in FIG. 2A. Thus, the angle of the radiopaque portion 30' may change relative to the patient and plane 62.

As illustrated in FIG. 2A, an image of the radiopaque member 30' is illustrated when positioned at an angle, and not parallel, relative to the plane 62. Again, as illustrated in FIG. 2B, the radiopaque portion 30' can be formed along an axis 30x that is positioned at an angle 70, which may be different than the angle 60, relative to the ray 40 of the x-rays. The angle 70 also gives rise to the complementary angle 71 relative to the plane 62. This also positions the radiopaque portion 30' at an angle relative to plane 62. As specifically illustrated in FIG. 2B, an end 72 of radiopaque portion 30' is angled out of plane 62. The end 72 of the radiopaque portion 30' may be a right end relative to the ray of the x-rays 40 out of plane 62 and towards the source 42. The right end 72 can be a distal end 72a illustrated in the image in FIG. 2A. A proximal end 74 is not as far out of plane 62 and can be a proximal end of the instrument, such as generally the proximal portion 74a in the image. The proximal end 74 may also be a left end or left portion of the radiopaque portion 30' relative to the ray of the x-rays 40 towards the receiver 44.

When an image of the radiopaque portion 30' is obtained when the radiopaque portion 30' is angled, as illustrated in FIG. 2B, the radiopaque portion 30a will have a unique configuration in the image illustrated in FIG. 2A. For example, an "u"-shape or "u"-valley 76 will appear in the image. The "u"-shape 76 is one of the valleys at 52 between two of the peaks 50 of the radiopaque portion 30'. The image of the radiopaque portion 30a at or near the end 72a coming out of the page or screen will appear to the user or an analysis system to include the "u"-shape and have substantially sharp peaks adjacent the "u"-shape 76. Accordingly, a user can understand that the radiopaque portion 30', and as a consequence the instrument 20, is oriented as coming out of the page of the two-dimensional image, as illustrated in FIG. 2A. Accordingly, an orientation of the instrument 20 can be determined based upon the image acquired of the radiopaque portion 30', and as illustrated as 30a in FIG. 2A. This also leads to a simple cue, if the radiopaque portion image 30a appears as like a "u", the right end is coming out of the page or screen 21.

The dimension of the "u"-shaped portion 76, such as a distance 78 between two of the peaks 50 and other geometries, as discussed further herein, can be used to determine a specific amount of orientation or angle relative to the plane 62. For example, as illustrated in FIG. 2A, it can be calculated that the right end of the catheter 20a is at an angle of about 15° out of plane 62. This is also shown as the angle 71 in FIG. 2B.

Figure 3:
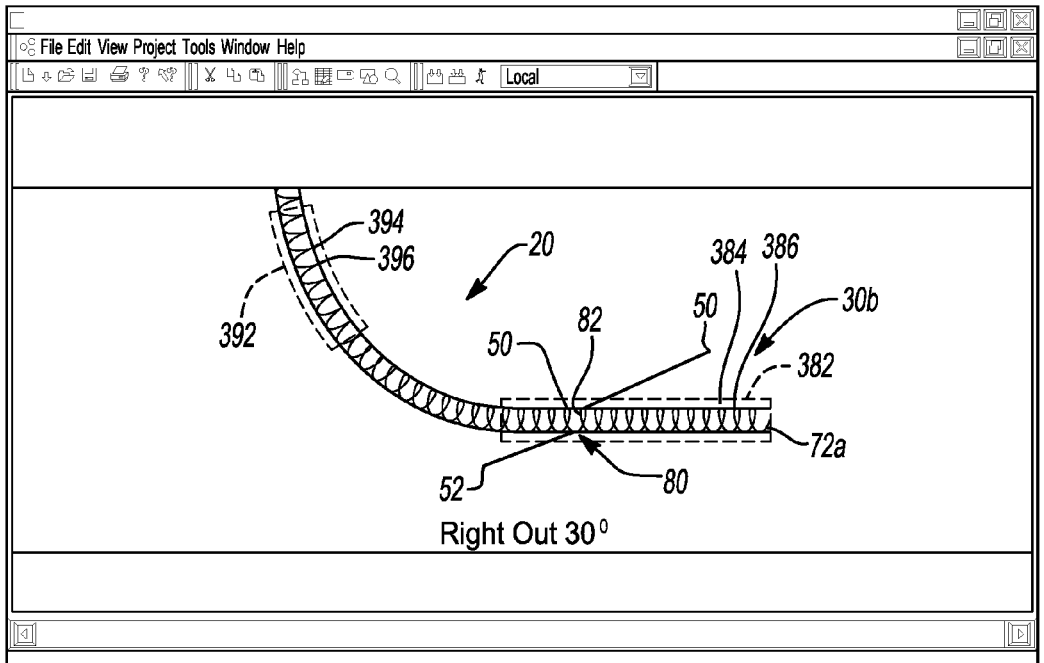
FIG. 3 is a screen shot of a display illustrating a configuration of an imageable portion for determining an angle of the imageable portion.

With reference to FIG. 3, a second "u"-shape 80 is illustrated. The "u"-shape 80 includes the valley 52 between two peaks 50. As illustrated in FIG. 3, however, the image of the radiopaque portion 30b is at an even greater angle out of the page. It can be determined to be at a greater angle out of the page due to at least the loops 82 near or at the peaks 50. As illustrated in FIG. 3, the loops 82 do not extend the entire width or diameter of the instrument 20 and have a small internal dimension circumscribed or surrounded by the loop portion. Accordingly, the user or an analysis system can determine that the right end 72a is extending at an angle about 30° out of the page or out of plane 62.

Figure 4:
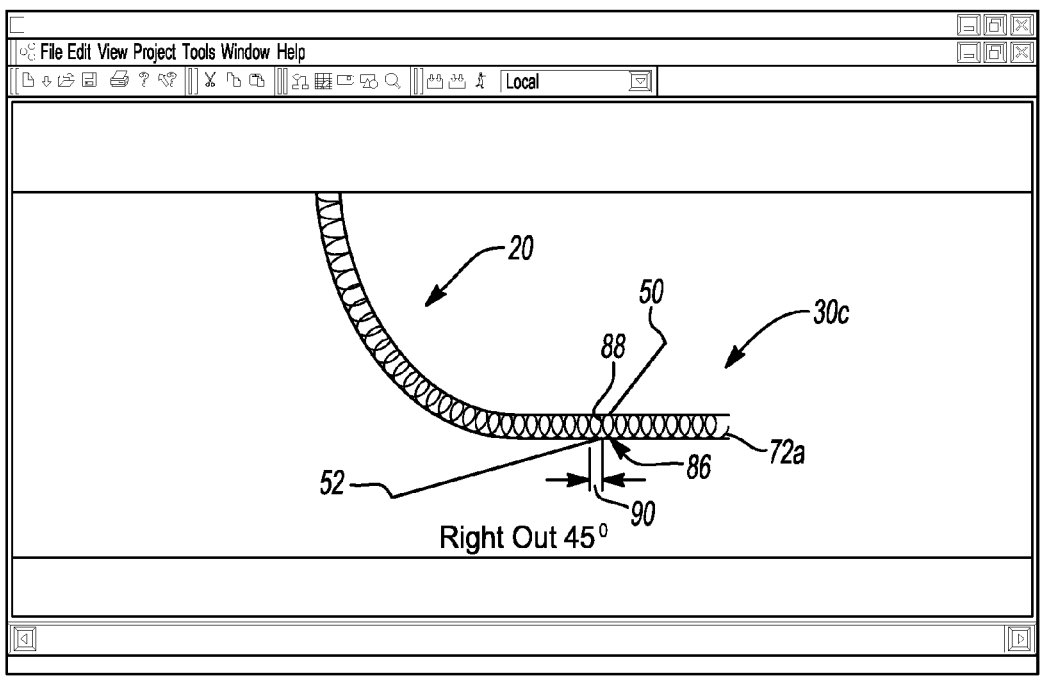
FIG. 4 is a screen shot of a display illustrating a configuration of an imageable portion for determining an angle of the imageable portion.

Finally, with reference to FIG. 4, a further example is illustrated where a "u"-shape 86 at the valley 52 is substantially smaller relative to large loops 88 at the peaks 50. The area within the loops 88 relative to a dimension of the "u"-shape 86, such as a width 90 of the "u"-shape 86, can be used to determine the angle of the right end 72a. For example, it can be determined that the right end 72a of the image 30c of the radiopaque portion 30' of the instrument 20a is at an angle of about 45° out of the page or out of plane 62.

Accordingly, it is understood that one skilled in the art and/or an analysis system can determine substantially precisely a location and/or an orientation of at least the radiopaque portion 30' that can be incorporated into the instrument 20a based upon the image of the radiopaque portion 30'. The angle of the radiopaque portion 30' can be used to determine orientation of the instrument 20. This orientation can be used to identify in a single frame, as illustrated in FIGS. 1-4, the three-dimensional position of the instrument 20. In other words, all of an x, y, and z position can be determined in a single image due to the inclusion of the radiopaque member 30' in the instrument that can be viewed as the image portion 30-30c.

Further, with reference to FIGS. 5A-7, a similar analysis can be used to determine that the right end of radiopaque portion 30' is angled in to plane 62. That is, the right end of radiopaque portion is angled in to the page. This is generally, and herein, referred to as a negative angle.

Figure 5A:
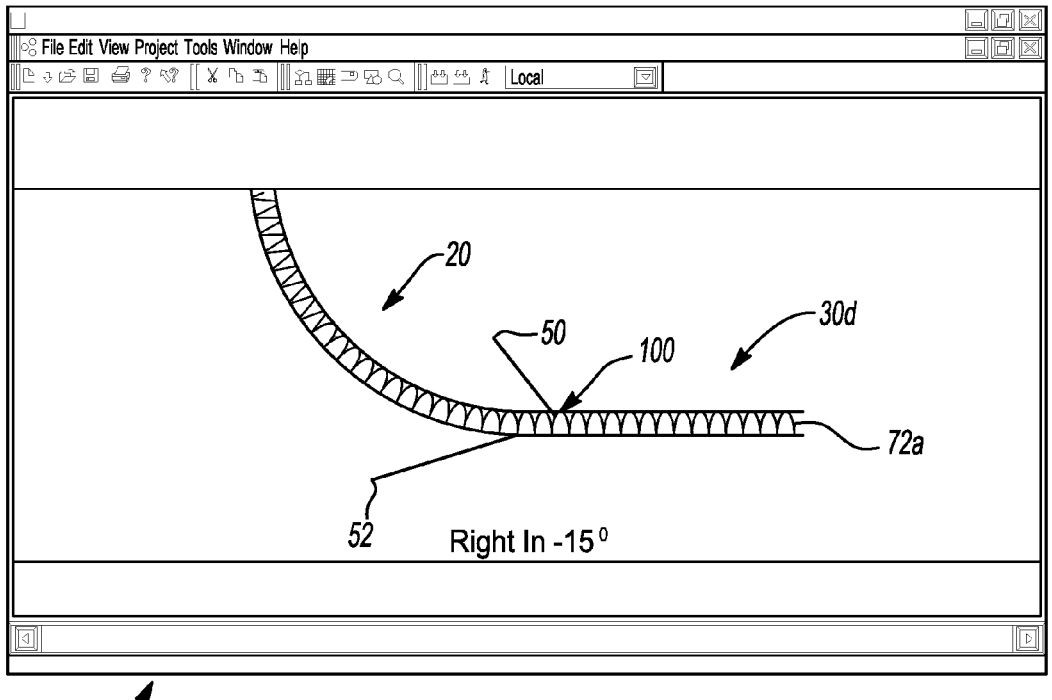
FIG. 5A is a screen shot of a display illustrating a configuration of an imageable portion for determining an angle of the imageable portion.
Figure 5B:
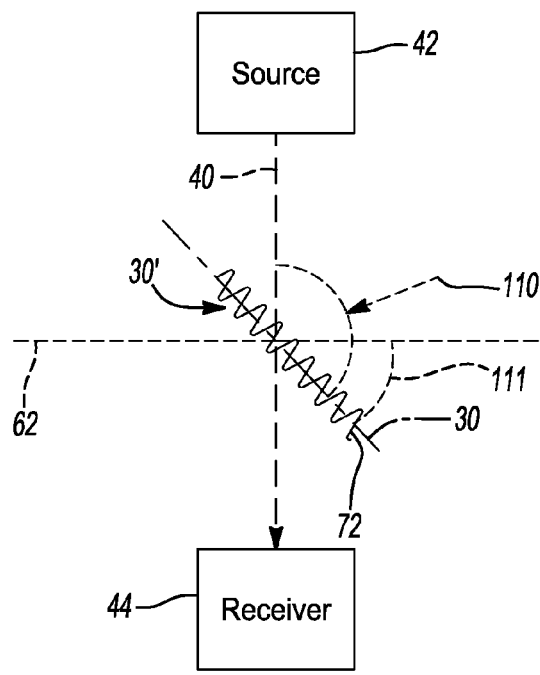
FIG. 5B is a schematic representation of an imaging system to generate the view of the imageable portion and its orientation relative to the imageable portion.

With reference to FIGS. 5A and 5B, a "n"-shape 100 can be defined or formed at the peak 50 of the radiopaque member 30' in the image 30d of the radiopaque member 30'. The "n"-shape may also be referred to or observed as an inverted "u" shape. The "n"-shape is the peak 50 between two consecutive valleys 52. As illustrated in FIG. 5A, the "n"-shape 100 is substantially gradual at the peak while having sharp valleys 52 between the peaks 50. Accordingly, in such a configuration, the user or an analysis system can determine that the distal end 72 of the radiopaque member 30' is going in to plane 62. When going into the plane 62 the radiopaque member 30' may be at an angle 110 relative to the ray 40 of the x-rays from the source 42 which gives rise to a complementary angle 111 relative to the plane 62. According to an analysis of the image 30' including the "n"-shape 100, it can be determined that the right end of radiopaque member 30', and the instrument 20 is angled at about 15° in to the page or in to plane 62. This also leads to a simple cue, if the radiopaque portion image 30a appears as like a "n", the right end is going in to the page or screen 21.

Figure 6:
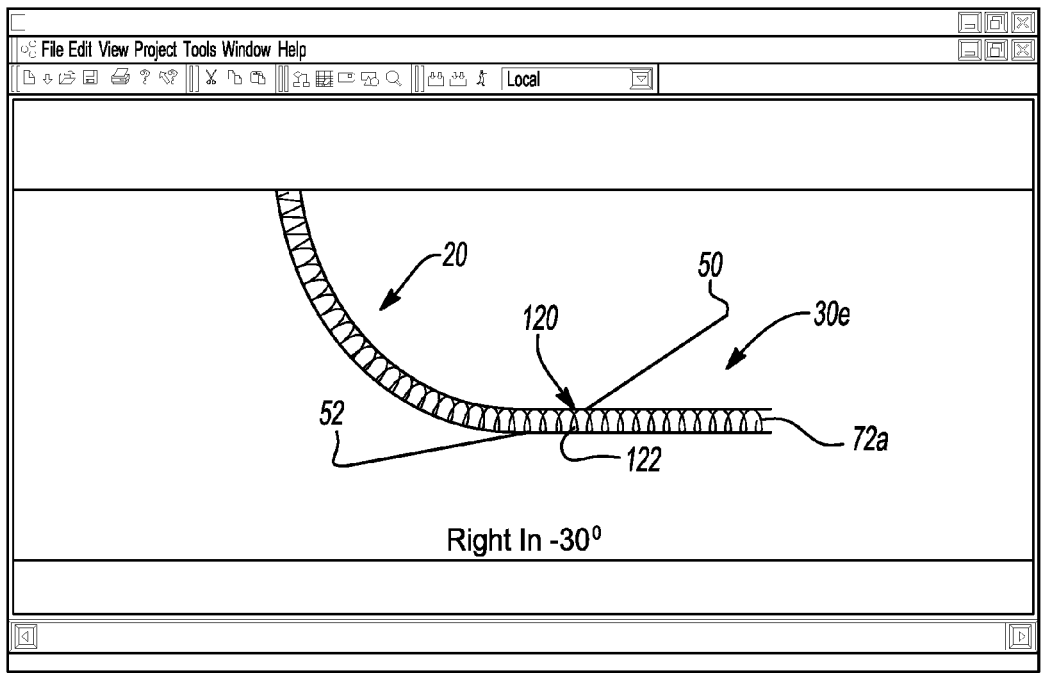
FIG. 6 is a screen shot of a display illustrating a configuration of an imageable portion for determining an angle of the imageable portion.

With reference to FIG. 6, an "n"-shape 120 can be formed or defined by the peak 50 between consecutive valleys 52 of the radiopaque member 30', as illustrated in the image 30e. Further, small loops or loops defining a small internal volume 122 can be illustrated at the valleys 52. Analysis of the image of the radiopaque portion 30e can determine that the radiopaque portion 30' and the instrument image 20 (which relates to the instrument 20) is generally at an angle of about 30° in to plane 62.

Figure 7:
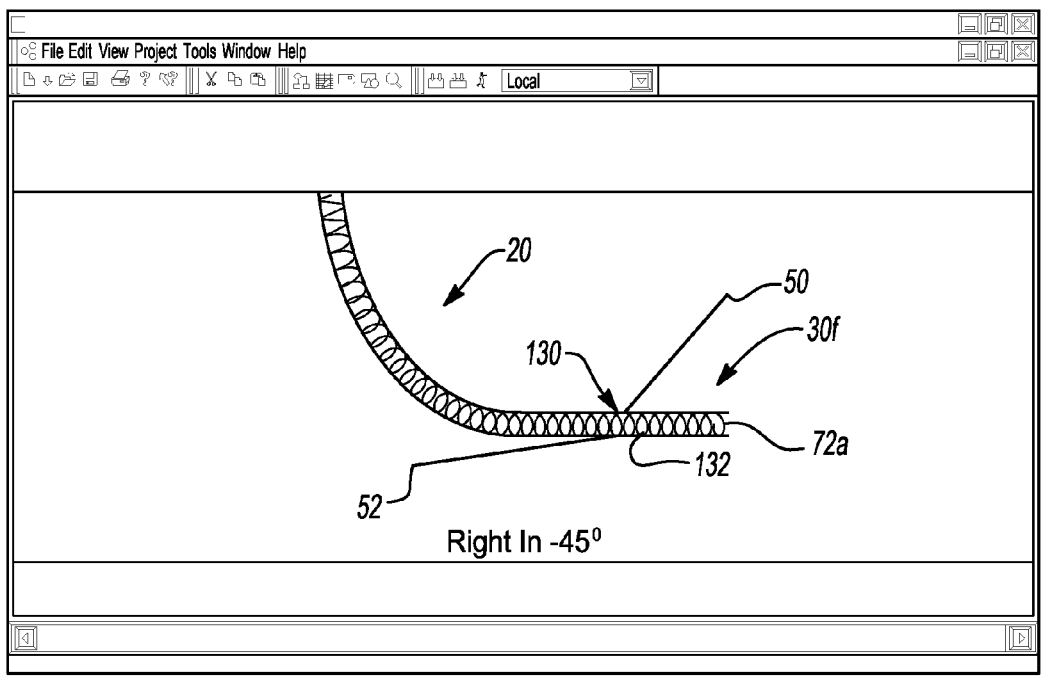
FIG. 7 is a screen shot of a display illustrating a configuration of an imageable portion for determining an angle of the imageable portion.

Finally, with reference to FIG. 7, an "n"-shape 130 can have a small area at the peak 50 between two of the consecutive valleys 52. Further, an area or volume within a loop 132 can be larger, as also shown in the image 30f of the radiopaque member 30'. An analysis or determination of a position due to the image 30f of the radiopaque portion 30' can determine that the instrument 20 and the radiopaque portion 30' is angled at about 45° in to plane 62, which is illustrated on the screen 21 as in to the page or screen.

With reference to FIGS. 1A, 2A, and 5A, it is understood that the receiver 44 and the source 42 can be oriented in any appropriate manner relative to the radiopaque portion 30'. For example, the source 42 and the receiver 44 can be inverted such that the receiver 44 is above the source 42. In this example, the source may be closer to a floor or base (e.g., below an operating table or platform) and the receiver 44 may be closer to a ceiling (e.g., above the operating table or platform on which a subject can be placed). It is understood, however, that the orientation of the radiopaque portion 30' relative to the receiver 44 (and plane 62) remains the same as discussed above. If the receiver is opposite than illustrated, however, then the image on the screen will be reversed. In typical use, the source is below the operating table and the image is flipped to provide the desired image (e.g., the patient's head on the top of the screen and the patient's left on the right of the screen). This has the same effect as viewing an image where the source is above the operating table.

In the specific embodiment illustrated in FIGS. 1A-7, the radiopaque portion 30 is formed as a right-hand coil helix. In the illustrated embodiments, as illustrated above, if the radiopaque portion image 30 looks like a "u", the right side of the image 30 is coming out of the page or screen which correlates to the right side of the radiopaque portion 30' coming out of the plane 62. This is true if the right of the display is the distal tip of the radiopaque portion 30' or the instrument 20a or the other end of the radiopaque portion 30' or the instrument 20a. Thus, if the right side looks like a "u" it is out of the screen 21. In a specific embodiment, such as within a human patient, the shapes and configurations, as discussed above and illustrated in FIGS. 1A-7, and shown in the image on the display 21 will have the radiopaque portion 30' or the instrument 20a pointing to the viewer's (e.g. user) right and the patient's left and the patient's head is toward the top of the image on the display 21.

It is understood, however, that the radiopaque portion 30' can also be a left-hand coil helix. The image relative to the receiver would then simply be reversed for determining the orientation relative to plane 62. Accordingly, the analysis and conclusions, as discussed herein, regarding the position and orientation of the radiopaque portion 30' can also be reversed for a left-hand coil configuration.

Additionally, the coil helix may be constructed at various and different selected pitches to, at least in part, optimize the sensitivity for a given clinical use condition. Also, the diameter of an instrument including the helix coil (e.g. a catheter) may affect the diameter of the helix coil, and in turn the pitch to ensure appropriate resolution in viewing the helix coil in the image. Also, the diameter of the coil may be independently chosen relative to the instrument.

In various embodiments, as illustrated in FIGS. 8A and 8Aa one helix coil 30j may have an outside diameter 30ja of about 0.12 inches with a pitch 30jb of about 0.21 inches and a coil angle 30jc of about 30 degrees (where the coil angle is relative to a line 63 that is perpendicular to a central axis 30jd of the coil helix 30j). In this configuration, the helix coil 30j will look like the "u" or "n", as discussed above, when the coil is positioned at an angle 30je of 30 degrees relative to the plane 62. When a helix coil 30k, as illustrated in FIGS. 8B and 8Bb however, has an outer diameter 30ka that is about 0.07 inches, a pitch 30kb may be about 0.013 inches to have the same resolution in the image as does the helix coil 30j, that is to view the "u" or "n" as discussed above. That is, at an angle 30jd that is a 30 degree angle relative to the line 63, the helix coil 30k with a smaller outer diameter may be required to have a shorter pitch to have the same resolution and/or image as the helix coil 30j with a larger outer diameter to view the "u" and "n", as discussed above. Further, to maintain the coil angle at a selected angle (e.g. 30 degrees) as the coil diameter changes, the pitch may also need to change, as illustrated in FIGS. 8A and 8B and discussed above.

In various embodiments, where the coil angle is 30 degrees, as illustrated in FIGS. 8A-8Bb, a fluoroscope may be positioned into an anterior-posterior (AP) position. In this orientation, the instrument including the coil helix 30j or 30k will appear as an "n" in the image. When the helix coil 30j or 30k is maintained in the orientation to appear as an "n" then it is easier to find a coronary sinus (CS) ostium in a human patient The helix coil 30, according to various embodiments may also be formed of a substantially radiopaque material. For example, a material such as gold, platinum/iridium, or a polymer loaded with at least 75% tungsten. Such substantially radiopaque materials may assist in resolution, such as a higher contrast, of the image of the coil helix 30. The radiopaque helix coil 30 may be surrounded by materials that are not very radiopaque to help ensure higher contrast for efficient visualization. Further, the geometry, such as a cross sectional geometry of the coil strand, of the coil helix may assist in resolution of the coil helix 30. Various cross-sectional geometries include hexagon, round, square, and trapezoid.

According to various embodiments, as illustrated in FIG. 9A, a radiopaque portion 140 can include a solid annular band portion 142 with one or more streamer or finger members 144 extending therefrom at a selected angle. The solid band 142 can be positioned at an orientation relative to a proximal or distal end of the instrument 20 and a user and/or analysis system (e.g., a processor executing instructions regarding a program to determine orientation of the instrument 20 based upon the image of the radiopaque member 140) can determine the angle of the instrument 20 based on the image of the radiopaque portion. For example, the solid portion 142 may be formed substantially concentric with a long axis of the instrument.

The position of the streamers 144 relative to the solid band 142 can be viewed and/or analyzed to determine an orientation of an end of the instrument 20. For example, as illustrated in FIG. 9A, if the streamers 144 are forming a V relative to the solid band 142, the right end of the instrument 20 is pointed out of a screen which relates to an orientation where the right portion of the instrument 20 is extending out of plane 62, similar to that illustrated in FIG. 2B. With reference to FIG. 9B, if the streamers form an inverted V relative to the solid band 142, it can be determined that the right end of the instrument, as illustrated on the page or screen, is pointing in to the screen or in to plane 62 as illustrated in FIG. 5B.

The various displays or screenshots illustrated in FIGS. 1A-9B and discussed above can be displayed on an appropriate display device, including a display device 230 illustrated in FIG. 10. The device 230 may have a display screen 232. It is understood that although the device 230 is illustrated as a substantially portable or tablet display device 230, the display screen 232 can be any appropriate display screen, such as a display screen of a computer, including a generally known laptop, work station, or the like. Nevertheless, the displays illustrated in FIGS. 1A-7 can be displayed on the display screen 232. Further, the display screen 232 can include other image data, such as an image of a heart 210 or other anatomical portions. Further, the device can include or be in communication with a processor 260 (such as a programmable computer processor) and a memory system 262 (such as a solid state or magnetic media memory system).

With additional reference to FIG. 10, an image of a heart 210 is illustrated for viewing on a display device 230. The image 210 may be a three-dimensional reconstruction of a heart so that the image 210 can be viewed from different angles or may include at least one two-dimensional (2D)

view, such as acquired with a fluoroscope. Further, a three-dimensional reconstruction can allow various measurements between two or more points to be made and/or compared. For example, a diameter of a vessel can be measured in the image 210. Further, the image 210 can include locations or landmarks that have been identified by a user and/or landmarks that have been identified based on statistical analysis of one or more subjects. For example, a database of one or more images of a heart can be used to provide and determine a statistically probable location and orientation of a coronary sinus ostium (CSOs) 250 relative to one or more landmarks that are predetermined and saved in the statistical analysis and can be identified by the user in the subject.

The image 210 can include various anatomical features which can be identified as landmarks or known to a cardiac surgeon (e.g. as discussed further herein), including an aorta 212, a left atrium 214, a left ventricle 216, a right ventricle 218, and a right atrium 220. Various other anatomical features may include an annulus of a valve, a coronary sinus (CS) 224 and/or the CSOs 250. The image 210 may also include vessel structures leading to the heart and may be displayed on the display system 230. The display system 230 can include a display device or screen 232, input buttons or portions 234, and a case 236. The display device 230 can include a touchscreen that allows a user to touch the screen 232 with a digit 240 to input commands, such as identifying one or more target locations. A hand 242 of the user may also be used to hold a tablet or handheld computing device including the memory and processor portions discussed above and/or able to access memory or processing systems.

Accordingly, it is understood that a radiopaque portion according to various embodiments, including the helix 30' or the radiopaque ring and streamers 140 can be designed and incorporated into the instrument 20 to allow for determination of an orientation of the instrument 20 relative to the screen 232, which can relate to an orientation of the radiopaque portion relative to plane 62. A processor for determining the orientation of the radiopaque portion relative to plane 62 is discussed further herein as an algorithm that can be incorporated into instructions that can be included in a program to be executed by a processor system, such as a processor system incorporated with a work station and/or computer, including device 230.

Three-Dimension (3D) Location Determination

With reference to FIG. 11, a method 300 is illustrated for at least determining and displaying a location and orientation of the instrument 20, as illustrated in FIGS. 1-9B. The method 300 can be incorporated into a computer program or code that can be executed by a processor system or computer system to analyze image data to, thus, determine and illustrate a location of the instrument 20. Accordingly, it is understood that the method 300 can be incorporated into an algorithm as a set of instructions to be executed by a processor system. The method 300 can also include various subparts or subroutines that include various program details, as discussed further herein.

Generally, the method 300 can include starting in block 302. Image data can be acquired in block 304, such as fluoroscopic or x-ray image data. The image data acquired in block 304 can be substantially real time image data (i.e. during a procedure and substantially instantaneously relative to a user's movement of the instrument). It is understood, however that the image data may be acquired by being recalled from a storage system. Generally, it is understood that fluoroscopic or x-ray image data can be substantially two-dimensional image data. The image data is generated by collecting x-ray energy on a substantially two-dimensional panel and is then displayed on a display device. An x-ray imaging device can be any appropriate imaging device. As illustrated above in FIGS. 1B, 2B and 5B, the receiver 44 can receive x-rays emitted by a source and generate a two-dimensional image as is generally understood by one skilled in the art. Various fluoroscopic or x-ray imaging systems can include the Innova imaging and guidance system sold by GE Healthcare, the Artis Zeego® imaging system sold by Siemens, the AXIOM Artis imaging system sold by Siemens, Allura® Xper imaging system sold by Philips, the Integris Allura® sold by Philips, and/or the Infinix® imaging system sold by Toshiba. Accordingly, the operation of an x-ray or fluoroscopic imaging system will not be described in further detail here.

An object or region of interest of an object can then be determined in block 306. As discussed further herein, various processes or steps can be used to determine the region of interest in the image. For example, a distal tip of a catheter or a distal tip of any appropriate instrument, such as the instrument 20 can be determined and identified as the region of interest (ROI). According to various embodiments, the distal tip can include the helix or radiopaque portion 30' that can be identified in the image data acquired in block 304.

After the ROI is determined, the ROI can be analyzed in block 308. The analysis of the ROI of block 308 can include determining a location, orientation, and other selected features within the image data. Again, the analysis can be performed using various methods, as discussed further herein. The analysis can then allow for a determination and display of a location and/or orientation of the instrument 20 in block 310. The method can then end in block 312. Accordingly, it is understood that the method 300, as illustrated in FIG. 10, can be used to acquire image data and determine the location/orientation of an instrument, including at least the distal tip of the instrument 20. The location/orientation of the instrument may also be displayed relative to an image of a heart, whether an atlas image or acquired of the patient. As discussed herein, the user can identify landmarks in the patient. The identified landmarks may be used to register an atlas to the patient and the determined orientation of the instrument may be illustrated relative to the displayed atlas image. For example, FIGS. 20 and 21 exemplarily illustrate a heart image relative to the imaged portion of the instrument 20a.

With reference to FIG. 12, locating the ROI in block 306 can include various subparts or subroutines illustrated in FIG. 12. Accordingly, it is understood that block 306, illustrated in FIG. 10, can include the subroutine portions illustrated in FIG. 12. The subroutine portions of block 306 can include identifying an object that is moving in the image data acquired in block 304, as specifically shown by identifying objects that are moving in block 320. Identifying objects that are moving in block 320 can include analyzing a series of image frames acquired over time, such as in a sequence. It is understood that a fluoroscope can continually acquire or acquire a plurality of images at a set interval. The plurality of images can be acquired automatically or by selection from a user, such as a surgeon.

The plurality of acquired images can be compared to one another to determine a portion or identify a portion in the image (e.g. an instrument) that is moving or changing within the plurality of images. As illustrated in FIG. 1B, the source 42 and the receiver 44 can remain or be positioned substantially fixed in space while the radiopaque portion 30', which can be included or attached to the instrument 20, can move. Accordingly, the identification of the moving portion can be identified in block 320. The moving portion can be identified by determining a difference between at least two, and including a plurality, of the image frames. The processor system, using generally known image analysis instructions, can identify or determine differences, such as changing contrasts or radiopaque regions, in a plurality of images.

The moving object can then be analyzed in block 322. The analysis of the moving object can include determining a specific shape or coil signature, including a relative or absolute width, length, or other geometry of the coil or other radiopaque portion 30', or other appropriate features of radiopaque portions. As illustrated in FIG. 1A, for example, and also illustrated in FIGS. 2A-9B, the radiopaque portion can appear in the image data. The radiopaque portion can be analyzed for the various features to specifically identify location of the selected radiopaque feature, such as the helix or radiopaque portion 30'. Thus, the analysis of the moving part in block 320 can be used to identify possible locations in the instrument 20. The identification of the ROI, including the radiopaque portion may include recalling, such as from a memory system, expected or saved characteristics of the radiopaque portion, including the helix 30'. Thus, saved features or expected geometries can be used to determine or select a possible ROI that can include the distal end of the instrument 20 that includes the radiopaque portion, such as the helix 30'.

Finally, identifying the ROI can occur in block 324. Identifying the ROI can be identifying the specific region of interest based upon the analysis of the moving object and the analysis and identification of specific characteristics of the radiopaque portion. Further, the identification of the ROI can include the specific and pre-determined features or characteristics of the radiopaque portion, including the helix 30'. For example, it can be pre-determined or known that the radiopaque portion, including the helix 30', can be 5 cm in length and 5 mm in diameter. Accordingly, the specific ROI, which can include the limited geometry of the radiopaque portion, can be identified in the image data that has been analyzed for movement.

It will be understood that if a portion or region of the image data that is determined to be moving in block 320 does not match an expected characteristic of the radiopaque portion of block 320, additional regions of the image data can be analyzed to attempt to determine moving portions of the image data, as shown in the loop 330. Further additional image data can be acquired to assist in determining portions of the image that may be moving between a plurality of the image frames. Further, if a region of interest cannot be identified in block 324, a loop 332 can be used to loop back to analyze moving objects to attempt to determine those that match the characteristics of the radiopaque portions and for determining terminal ends and external geometries of the radiopaque portion.

With reference to FIG. 13, the analysis of the ROI in block 308, is illustrated and can be used to identify a three-dimensional location of the instrument 20, including the radiopaque portion 30'. Thus, analyzing the ROI in block 308 can include the sub-routing illustrated in FIG. 13. Further, the subroutine can be incorporated into instructions executed by a processor, as discussed above.

According to various embodiments, the analysis of the region of interest can include determining a direction of the instrument 20 in a X and a Y plane in block 340 and determining a direction of the instrument in a Z plane in block 342. It is understood that determining a direction of an instrument in an XY plane can include various subroutines, as discussed further herein, and the determination of the direction of the instrument in the Z plane in block 342 can also be incorporated into various subroutines.

Initially, the XY plane can be the plane of the image acquired with the imaging system, such as the fluoroscope or C-arm as discussed above and illustrated in FIGS. 1A, 2A, and 5A. For example, with reference to FIG. 1A, the XY plane can relate to the plane of the page or screen. This is also known as plane 62 in FIG. 1B. Further, the acquisition of the image, such as the image illustrated in FIG. 1A, can be acquired knowing an orientation of an imaging system, such as a C-arm, relative to a reference point, such as the plane or top of a platform on which a subject is placed.

Once the XY plane is determined or analyzed, a centerline of the ROI determined in block 384 can be determined. Various techniques can be used to determine the centerline, such as identifying an extent of radiopaque boundaries, such as 346 and 348, illustrated in FIG. 1A. The extent of the boundaries can be based on known dimensions of the radiopaque portion 50 and/or calculations of the geometry of the ROI based upon the image. The centerline can be a line that is equal distance between the two boundaries 346 and 348 and can be identified as a centerline 350. An angle of the centerline 350 relative to a vertical axis 352 can be made to calculate or record the angle of the centerline in block 354. The recorded angle of the centerline 350 relative to the axis 352 can also be recorded in context when the angle orientation of the imaging system is known, such as an imaging plane of the C-arm (e.g., plane 62).

Accordingly, the direction of the instrument 20, such as defined by a ray towards a right end or distal end 360 of the instrument 20, including along the centerline 350, can be determined. Thus, the direction of the instrument 20 in an XY plane relative to the vertical axis 352 can be known. As discussed above, also a Z direction or a direction of the instrument 20 relative to the Z plane can be determined in block 342. As discussed further herein, this allows for a three-dimensional position of the instrument 20 to be determined by analyzing the view of the imager, such as that illustrated in FIG. 1A.

Determining a direction of the instrument in the Z plane can be determined in block 342 including the subroutine as discussed further herein. Initially, the geometric shape of the radiopaque portion 30, such as including coils illustrated in FIGS. 1-7 and 8A-8Bb, can be determined in block 364. This can include an interpolation between radiopaque (i.e., dark or high contrast) pixels in the image. As the viewable or analyzed geometry of the radiopaque portion 30 assists in determining an orientation of the instrument 20 relative to the image plane XY, it can be selected to create as complete as possible shape of the radiopaque portion 30. Accordingly, the radiopaque portion 30 can be identified as the high contrasted pixels and an interpolation between the identified or dark pixels can be made to ensure as complete as possible geometry of the radiopaque portion 30 is determined.

After the geometry of the radiopaque portion 30 is determined in block 364, the determined geometry from block 364 can be compared to reference images in block 366. The comparison to reference images can include a comparison of the recreated geometry from block 364 to reference images, including those illustrated in FIGS. 1-8Bb. The reference images can be previously acquired, analyzed and saved images or theoretical images of the radiopaque portion in different orientations relative to plane 62. As discussed above, FIG. 1A illustrates the geometry of the radiopaque portion 30 when it is at substantially 0° angle relative to the plane 62. FIG. 2A illustrates a geometry of the radiopaque portion 30 when it is 15° out of plane 62. Accordingly, a comparison of the determined geometry in the image currently acquired (e.g. during a procedure or any image acquired for analysis) can be made to reference images of the geometry of the radiopaque portion 30 at different angles relative to plane 62.

It is understood that the greater the number of reference images between the different angles for comparison, the greater the accuracy of the angled determination can be made. For example, the difference between FIG. 1A and FIG. 2A is 15°, but an additional reference image that is, for example, half of the difference between FIG. 1A and FIG. 2A, can illustrate the geometry of the radiopaque portion 30 at the 7.5° out of plane 62. Accordingly, comparison to reference image or images can allow for a determination of an angle based upon the fineness or the number of reference images.

Nevertheless, this comparison allows for a determination of the Z-direction angle of the instrument 20 in block 370. A best fit or best match to a single reference image can be made to determine the angle. Further, it is understood, that an interpolation between two reference images can be made to estimate an angle, if the determined geometry of the radiopaque portion 30 in block 364 does not match substantially identically (e.g., within about 5%) of one of the reference images. Further, it is understood that reference images can be stored in a database that is stored in a memory system 260 retrievable by the processor 262 executing the analyzing the region of interest in block 308.

Accordingly, the display of the direction of the instrument 20 can be made in block 310 on a display device, such as the display device 232 illustrated above. It is further understood that the illustration can be made at any appropriate display device, including a printout, computer display, or other appropriate display. Further, the display can include not only a graphical representation of the instrument 20 and/or the radiopaque portion 30, as illustrated in FIG. 1A, but can also include a numerical output, such as 0° or right out 15°, as illustrated in FIGS. 1 and 2, respectively.

According to various embodiments, with reference to FIG. 14, the determination of the instrument 20 in the Z plane can be determined, as illustrated by block 342'. It is understood that the determination of the direction of the instrument in the Z plane, as illustrated and discussed in block 342 in FIG. 13 above is appropriate and that alternative and/or additional embodiments can be used to determine the direction of the instruments in the Z plane, such as in block 342' in FIG. 14. Thus, with reference to FIG. 14, the determination of the direction of the instrument 20 in the Z plane can be made based upon a calculation of a determined angle and/or geometry of the imaged radiopaque portion 30' without comparison to reference images. As discussed in block 366 above, the determination of an angle of the instrument 20 can be made by comparison of an acquired image during a procedure to a previously acquired or determined reference image. It is understood, however, that a calculation based upon the determined geometry of the instrument, including the radiopaque portion 30', in the instantly or procedure acquired image can be used to determine the angle of the instrument 20 in the Z plane. Accordingly, it is understood that the determination of the angle of the instrument in the Z plane in block 342', illustrated in FIG. 14, can be alternative and/or in addition to the determination made in block 342 illustrated in FIG. 13.

Initially, the image of the instrument, including the radiopaque portion 30, can be captured and the geometry can be captured and/or recreated in block 364 in a manner that is substantially identical to that discussed above. Accordingly the determination of the geometry of the radiopaque portion 30' can be substantially similar to capturing and recreating the geometric shape for comparison to a reference image as discussed above.

Once the geometry of the radiopaque portion 30' is recreated in block 364 a measurement of the period length of the coils in the region of interest can be made in block 380. With additional reference to FIG. 3, the ROI determined in block 324, as discussed above, can be illustrated as a boxed region 382 in FIG. 3. Within the region of interest in box 382, a period length of the coils can be measured. The period length can be a distance between two peaks, such as a first peak 384 and a second peak 386. A distance between the two peaks 384, 386 can be used to determine a period within the ROI 382. It is understood that the period between all of the coils can be measured within the region 382, if selected or any number thereof. Moreover a plurality of measurements can be made based upon the image, for example the image in FIG. 3, and the period calculation can be averaged to create an average length period. The determined or measured period length can be stored in the memory system for further calculation, such as the memory system of the processor system or computer system illustrated in FIG. 10.

A period length of the coils of the radiopaque portion 30', viewable within the image can also be measured for a proximal portion or a portion that is not within the ROI 382. For example, the proximal portion can include the left most portion of the radiopaque portion, or any portion that is left of a bend of the coil portion. As illustrated in FIG. 3 the proximal region can be identified by a box 392. Again, a period between two adjacent peaks 394 and 396 can be measured to determine a period length. Further, all of the period lengths within the proximal region 392 can be measured to determine a period length and a plurality of measurements can be made and an average period length can be determined. Further a longest period length can be determined in the proximal region 392 and can be used for further comparison, as discussed further herein. Moreover an assumption or predetermined period length can be made based upon a manufactured period length of the radiopaque portion 30'. Again, the instructions to determine a period length can be stored in the memory system, including that discussed above, and/or can be recalled for the memory system such as based upon a manufactured period length.

After determination or measuring of the period length of the coils in the ROI 382 and in the proximal region 392, a calculation of an arc cosine of the quotient of the period length of the ROI 382 over the period length of the proximal region 392 can be determined or made in block 400. Alternatively, the calculation of the angle can be the arc cosine of the ROI 382 length divided by the maximum period length in the proximal region 392, as discussed above, or the arc cosine of the tip period length in the ROI 382 divided by the recalled the manufacture period length of the radiopaque portion 30' which can be the assumed period length of the proximal region 392. Thus the angle of the tip in the ROI 382 can be calculated. Accordingly, in block 400 the angle of the instrument including the tip ROI 382 can be determined.

Once the angle is determined in block 400, a determination of a positive or a negative direction can be determined in block 410 using the herein described subroutine portions. The determination of the direction into or out of the page can be similar to the angle of the determinations or illustrations as discussed above in FIGS. 2-4 for out of the page (i.e., a positive angle) or in to the page illustrated in FIGS. 5-7 (i.e., in to the page).

The determination of whether the angle determined in block 400 is positive or negative, can include an evaluation of the coil shape in the ROI 382 in block 412. The evaluation of the shape can be based upon a comparison to a generally known shape or a calculated shape. As discussed above, and illustrated in the FIGS. 2A-4, if the angle is coming out of the page, or a positive angle, the shape of the radiopaque portion of the image is the "u" shape. If the angle is a negative angle, or going in to the page, as illustrated in FIGS. 5-7, the shape of the radiopaque portion of the image 30 is the "n" shape. Accordingly, evaluating the shape in block 412 and determining or identifying the shape is used to relate a negative or positive orientation in block 414 to the angle calculated in block 412. Accordingly, the angle of the radiopaque portion in the image can be determined in block 400 and the negative or positive angle can be made or determined in block 414. As discussed above, the determination of the angle and direction of the radiopaque portion of the catheter in the Z plane in block 342 can be in addition to alternatively to the determination of the direction of the instrument of the Z plane in block 340 discussed above in relation to FIG. 13. Accordingly, block 342' can be used in place of or in addition to block 342 in FIG. 13 discussed above. Also, it is understood that the method 342' can be incorporated into instructions to be executed by the processor 262.

With reference to FIG. 15, an alternative method for determining whether the angle determined in block 400, in FIG. 14, is negative or positive is illustrated in block 410'. As discussed above, various alternative methods can be used for determining the location and orientation of the distal end of the instrument 20, including the radiopaque portion 30'. According to block 410', illustrated in FIG. 15, a method to replace or be used as an alternative to the method 410 in FIG. 14 is illustrated and herein described. The block 410' for determining a direction that is positive or negative can include various subroutines and portions as discussed further herein. It is further understood, these subroutines can also be incorporated into instructions to be executed by the processor 262.

Initially, with additional reference to FIGS. 16 and 17, a determination of an exterior boundary of the radiopaque portion and the determined centerline 350 thereof, as illustrated in FIG. 1A, can be used to generate or determine an upper line 420 and a lower line. Illustrated in FIG. 16 is at least a portion that is a distal portion of the instrument illustrated in FIG. 2A, discussed above, including the ROI 382. The outer boundary of the radiopaque portion can be illustrated by a box 426, which can include all or a portion of the ROI 382. The illustration in FIG. 16 can be a screen capture or the image data acquired with the imaging system. Thus, the upper line 420 can pass through a plurality of pixels that have a high contrast or dark image pixel. Similarly, the lower line 424 can pass through a plurality of pixels that have a high contrast or dark image portion.

With reference to FIG. 17, a plot of the high contrast portions intersected by each of the lines 420, 424 can be made based upon the darkness or grey scale relative to a length along the region of interest. As illustrated in FIG. 17 for the "u" shape, the upper line 420 will have a lower frequency of high contrast pixels along the length of the region of interest than the lower line 424. As illustrated in the graph in FIG. 17, the lower line is illustrated by a high intensity image 424$i$ along the length of the ROI 426 of the instrument while the upper line is illustrated as a peak 420$i$ along the length of the ROI 426.

Accordingly, with continued reference to FIGS. 16 and 17 and returning reference to FIG. 15, the upper and lower lines 420 and 424 can be determined in block 430. The upper and lower lines, 420 and 424 can be used to capture a slice of pixels along the length of each of the two lines 420, 424 in block 432. A contrast analysis can be performed to count the number of radio-dense regions, as illustrated in FIG. 17, in block 434. A calculation can then be made in block 436 to determine the positive or negative nature of the angle determined in block 410, illustrated in FIG. 14. As illustrated in FIG. 17, a higher frequency of the lower line 424 compared to the upper line 420 generally relates to the "u" shape. Accordingly, if a higher frequency of the lower line 424 is determined in the analysis, as illustrated in the graph FIG. 17, it can be determined that the calculated angle is positive or out of the plane 62. As discussed above a "u" shape is related to a positive angle.

Illustrated in FIG. 18 is at least a portion that is a distal portion of the instrument illustrated in FIG. 5A. With additional reference to FIGS. 18 and 19, the ROI 426 can be taken relating to a distal end of the instrument 20 discussed and illustrated above. Again, the upper line 420 and the lower line 424 can be determined in block 430. Capturing of the pixels along the length of the lines can again be made in block 432 and a contrast analysis can be performed in block 434 as, illustrated in FIG. 19. As illustrated in FIG. 19, if the radiopaque portion 30' forms the "n" shape, the upper line 420 will have a higher frequency, illustrated as the peak 420$i$ in FIG. 19, than the lower line 424, illustrated as the peak 424$i$ in FIG. 19. Thus, a high frequency of the upper line 420 having a radio dense or high contrast frequency, as illustrated in FIG. 19, can relate to the "n"-shape which relate to a negative or in to the page angle.

Thus, it is understood, that alternatives and/or additional method for determining a positive or negative angle can be made in block 410' illustrated in FIG. 15. Accordingly, it is understood, that one or a plurality of methods can be used to determine both an angle and/or a positive or negative determination for the angle of the distal tip including the ROI 382 of the instrument 20. Further, it is understood, that the various methods discussed above, including those illustrated in FIGS. 11-15 can be incorporated into computer instructions for being executed by a processor or processor system, including the processor 262 illustrated in relation to the system in FIG. 10. Accordingly, one skilled in the art will understand that the various methods can be performed substantially automatically by a processor system based after the image data is acquired with an imaging system, as discussed above. Further, the analysis may be performed following data acquisition without requiring manual input or calculation, thus allowing the determination to be seamless or invisible to a user.

Anatomical Target Identification

According to various embodiments, a user, such as a surgeon including that discussed above, can identify various landmarks in a subject, such as portions of a heart 210, as illustrated in FIG. 10 on the display 232. The various landmarks can be determined based upon pressure differentials direction changes of an instrument, and a combination of tactile and visual cues. For example, viewing and evaluation of the images, including the images of the helix coil 30, may be used to assist in identifying an anatomical target. Evaluation of the images may be automatic, such as using various and known segmentation algorithms. Further, manual evaluation may be used to identify landmarks. For example, a surgeon's expertise may be used to identify anatomical landmarks in an image of a subject.

As understood by one skilled in the art, the instrument 20 can include various measuring portions, such as a pressure measuring system to measure a pressure at a selected position along the instrument 20. For example, a pressure measuring portion can be positioned near the distal end 72a of the instrument 20. As the user moves the instrument 20 through the heart, the user can view or be displayed pressures. When a pressure change occurs, a user can identify the portion of the anatomy related to the pressure change, such as a tricuspid valve or other feature. For example, if the instrument 20 is moved through a superior vena cava 233 of the heart 210 into the right atrium 220, the user can identify a pressure change between the superior vena cava 233 and the right atrium 220 and label the same on the display 232 or for other uses. The user can also identify other landmarks including electrical features based upon measurements of electrical physiology of the subject and these can also be labeled on the display 232 of the heart 210.

It is understood that any appropriate landmarks, as illustrated in FIG. 19, can be identified using various features such as pressure changes, electrical measurements and changes, and other measurable features (e.g. image contrast and density changes). Accordingly, various landmarks, such as a first landmark 240 can be identified. The first landmark 240 may be an ostium from the superior vena cava 233 to the right atrium 220. A second landmark 242 may be a tricuspid valve, which is between the right atrium 220 and the right ventricle 218. Other appropriate landmarks may also be identified, and the first and second landmarks 240, 242 discussed herein are merely exemplary. It is understood, soft tissue may not appear in high contrast in fluoroscopic images. Thus, the landmarks may appear to be shown in "empty space." Thus, the illustration of a heart in the various figures, including FIGS. 19 and 20, is for clarity of the current discussion and such an image of the heart may not be present on the display. As discussed above, however, the identified landmarks can be used to register or illustrate an atlas heart (i.e. a heart based on previously acquired image data and/or statistically typical heart) relative to the identified landmarks.

The landmarks identified by the user and saved in the memory system and/or related to various locations on the heart 210 can be used to identify other features of the heart. For example, a CSOs 250 may be a portion of the anatomy of the heart 210 and may be identified for various purposes. For example, as discussed above, cannulation of the CSOs 250 with the instrument 20 can be used for various portions of a procedure, such as placing a guide wire or placing the instrument 20 into a coronary sinus 224.

The user can identify various landmarks or reference structures on the image 210 to assist in triangulation and determination of a selected anatomical target, such as the CSOs 250. The various landmarks or reference structures can include the superior vena cava (SVC) ostium 240 and the tricuspid valve (TV) annulus 242. As discussed above, these various annulus or structures can be identified using appropriate techniques, such as a pressure measure system associated with the instrument 20, electro-physical information, or other appropriate techniques (e.g. visual and tactile techniques, as noted above). Thus, the image 210 can be used by the user to identify the various reference structures to allow for triangulation or determination of the location of the CSOs 250.

Triangulation of the CSOs 250 can be based upon various techniques, such as those disclosed in U.S. Pat. No. 7,797,030 to Lahm, et al., incorporated herein by reference. Generally, at least two reference structures can be used to identify a target in a subject, such as the CSOs 250. Further, it will be understood that the various landmarks, including the first and second landmarks 240, 242 can be identified without the use of the image 210 and only using the various techniques discussed above, such as electro-physiological data and/or pressure information obtained using the instrument 20.

With continued reference to FIG. 20, once the appropriate landmarks or reference structures have been identified such as the SVC ostium 240 of the superior vena cava 233 to the right atrium 220 and the tricuspid valve 242, triangulation of the CSOs 250 can occur. Triangulation, as is understood by one skilled in the art, is generally a mathematical technique to identify a location of a third point based upon two points. As disclosed in the U.S. Pat. No. 7,797,030, triangulation of the CSOs 250 can be performed by executing instructions stored in the memory system 260 that may be executed by the processor 262. Accordingly, one skilled in the art will understand that a set of instructions stored as a program can be executed by the processor 262 to triangulate the location of the CSOs 250 based upon the identification of the landmarks 240, 242.

The triangulation of the CSOs 250 can be based upon a predetermined triangulation of a specific patient, such as a patient on which a current procedure is occurring. According to various embodiments, image data or a previous procedure can be used to identify the anatomical landmarks, such as the superior vena cava ostium 240 and the tricuspid valve 242 along with a predetermination of the CSOs 250. The triangulated location of the CSOs 250 for the specific patient can then be stored in the memory system 260, or in an appropriate memory system, for being recalled to the processing system 262 for determination of the CSOs 250 during a current procedure, after the user identifies the landmarks 240, 242.

According to various embodiments, a statistical analysis of a population of such objects, such as human patients, can also or alternatively be used to identify a statistically probable location and orientation of the CSOs 250 relative to selected landmarks. Again, the landmarks may include the superior vena cava ostium 240 and the tricuspid valve 242. The statistical analysis can be performed on a population of subjects, such as with image data from the population of subjects, and a determined statistically valid triangulated location of the CSOs 250 can then be stored in the memory system 260. The statistically determined triangulated location of the CSOs 250 can be stored to and/or retrieved from the memory system 260 for processing by the processor 262.

Thus, the triangulation of the CSOs 250 based upon selected landmarks, including the first and second landmarks 240, 242 discussed above, and using selected triangulation calculations. The triangulation can be based upon a patient-specific triangulated or measured location of the CSOs 250 relative to the specific landmarks or based on the statistical analysis of the CSOs 250 location relative to selected landmarks. The location of the landmarks relative to the CSOs 250 can be determined and used for triangulating the CSOs 250 relative to landmarks identified by a user. Also, the landmarks can be selected based upon efficiently/or easily identified anatomical features such as the superior vena cava 240 and/or the tricuspid valve 242. Moreover, it is understood that the triangulation of the CSOs 250 in the selected subject can be incorporated into instructions that are executed by the processor 262.

In light of the above, and for example with reference to FIGS. 1A and 1B, the position and orientation of the instrument 20 can be determined in the image acquired of the subject and the instrument 20. The image of the instrument 20 can be displayed on the display device 232, for example as illustrated in FIGS. 20 and 21. The illustration of the instrument 20 can be based on an image acquisition of the radiopaque portion 30 of the instrument 20. As discussed above, the radiopaque portion 30 of the instrument 20 allows for a determination of an orientation and position of the instrument 20. Thus, the image being viewed on the display device 232 can include an image of the radiopaque portion 30 of the instrument 20 and other radiopaque or partially radiopaque portions, such as a heart 210, bone structures, or other radiopaque portions or structures of a subject.

It is understood that various portions of an anatomy, such as human anatomy, however, may not be as radiopaque as the radiopaque portion 30 of the instrument 20. Thus, the image of the heart 210 may be substantially faded or indistinguishable relative to the instrument 20 on the display device 232. Thus, the illustration of the heart 210 on the display device 232 in FIGS. 19 and 20 is for clarity of the current disclosure. Nevertheless, as discussed above, the landmarks 240, 242 can be identified by the user. The landmarks 240, 242 may also be displayed on the display device 232, such as relative to one another. Based upon the triangulation of a target, such as the CSOs 250, as discussed above, a possible or a statistically likely location of the CSOs 250 can also be displayed on the display device 232. Accordingly, a target icon 250i can be displayed on the display device 232 to illustrate a probable location of the CSOs 250. The display of the instrument 20, which may include substantially only the radiopaque portion 30, can be used by the user and/or the processor 262 to determine the selected location and orientation of the instrument 20 to access or to cannulate the CSOs 250. As discussed above, the 3D location and orientation of the radiopaque portion 30' can be determined by the various embodiments.

With continued reference to FIGS. 20 and 21, the position of the instrument 20 can be illustrated as a current or an instantaneous location of the instrument 20. The location of the instrument displayed on the display device 232 is displayed due to the radio-opacity of the radiopaque portion 30 and the view of the acquired image, including the radiopaque portion 30 within the image. Accordingly, the instrument 20 need not include other tracking features, such as electro-magnetic or optical tracking features including navigation and tracking features included with various navigation assistance, such as the StealthStation® S7® surgical navigation system which can include the AxiEM™ surgical navigation system. The location and orientation of the instrument 20 can be determined based on the procedures discussed above, such as those illustrated in FIGS. 1-19.

The display of the radiopaque portion 30 of the instrument 20 can be used to identify the instrument 20, according to the techniques discussed above. The images acquired with the imaging system, including the source 42 and the receiver 44, as discussed above, are used to view and determine the location and orientation of the instrument 20. Accordingly, instructions including the determination of the orientation and position of the instrument 20 can be executed by the processor 262 to determine the location and orientation of the instrument 20 relative to the probable location of the CSOs 250 that can be illustrated with the icon 250i.

Further, the processor 262 can provide suggestions for movements and/or changing orientation of the instrument 20 relative to the probable CSOs location/orientation identified by the icon 250i. For example, a display box 270 can be displayed on the display device 232 to illustrate suggested or possible movements of the instrument 20 to achieve proper cannulation of the CSOs 250. For example, the suggested movement box 270 can include suggested movements such as "Rotate out 20", which may be an instruction to the user to rotate the instrument out of the plane by 20 degrees. Other instructions may include "Move superior 5 mm", which can be an instructions to the user to move the instrument superior 5 millimeters (mm) from the current location. If the instrument is adequately close to the CSOs 250, but not in alignment with it, the system could suggest that the user rotate the instrument appropriately in order to align with the CSOs 250. The suggested orientation and movement of the instrument 20 suggested by the movement box 270 can be determined due to the determined location and orientation of the instrument 20 displayed due to the radiopaque portion 30 in the image and the probable CSOs location/orientation 250i.

In addition to the suggested movement box 270, a suggested movement arrow or icon 274 may also be illustrated, or may be illustrated in an alternative to the suggested movement box 270. The suggested movement icon 274 can illustrate a direction and orientation of the instrument 20 that may be different from the current location of the instrument 20 illustrated by the image of the radio opaque portion 30 on the display 232. A user can then move the instrument to achieve the suggested movement icon 274 and continuously acquire new images of the radiopaque portion 30 for display on the display device 232 and to determine the current location and orientation of the instrument 20.

Accordingly, the system, including the processor 262, can generate and display icons to provide suggested movements of the instrument relative to the probable location of the CSOs 250 illustrated by the icon 250i. In addition, assistance for cannulating the CSOs 250 may include illustrating previous locations of the instrument 20 relative to the probable location icon 250i. As the image of the instrument 20 is acquired over time, each new image will illustrate only the current location of the instruments due to the radio opacity of the radiopaque portion 30. Accordingly, the system, including the processor 262, can illustrate or generate icons 280, shown in FIG. 20, that illustrate previous locations of the instrument 20 based upon previous images of the radiopaque portion 30.

The icons 280 illustrating previous locations of the instrument 20 can be selectively illustrated by the user. The icons 280 can be illustrated in any appropriate manner, such as illustrated in a generally "L"-shape which may mimic the shape of the instrument 20, or at least the radiopaque portion 30. The number of the previous location icons 280 can also be selected by the user, such as identifying a past five locations, past ten locations, or any appropriate number. The past number of locations can also be a time span, such as illustrating the past locations of the instrument 20 for five seconds, ten seconds, twenty seconds, or any appropriate time span.

The user can view the prior locations of the instrument 20 as the icons 280 and determine if a portion of the area around the probable location of the CSOs 250 illustrated by the icon 250i has not been explored. As illustrated in FIG. 20, the icons 280 illustrate that a region superior to the icon 250i has not been explored with the instrument 20. Accordingly, the user may select to move the instrument 20 to a more superior location to attempt to cannulate the CSOs 250. Similarly, the instrument may in fact be at the CSOs 250, but based on information such as a color-coded indicator, the user may receive feedback that the catheter orientation does not align with the probable orientation of the CSOs 250. The user may then be prompted to apply a certain rotation to the instrument in order that both location and orientation of the instrument match well with the probable location and orientation of the CSOs 250 and coronary sinus. As discussed above, the icon 250i illustrates a probable location of the CSOs 250 based upon statistical analysis. It is understood, however, that a patient may have a location of a CSOs 250 that is slightly outside or not at the probable location based upon a selected population of subjects. Accordingly exploration of the anatomy may be required to achieve cannulation of the CSOs 250.

It is further understood that additional exploration techniques can be used, such as "puffing" a contrast agent from the instrument 20. Once the instrument 20 is positioned near the probable location illustrated by the icon 250i of the CSOs 250, a contrast agent can be puffed out of the instrument 20. A small amount of contrast agent can be viewed on an image on the display device 232. A viewed movement or direction of the contract agent can be used to determine whether a flow of blood is occurring from the CSOs 250 in a selected location. Analysis of the flow of the contrast agent can be performed to assist and identify a probable location of the CSOs 250. The processor 262 can analyze a flow of the contrast agent from the instrument 20, illustrated as the radiopaque portion 30 on the display device 232, to assist in identifying suggested movements that can be displayed as the suggested movement box 270 and/or the suggested movement icon 274.

In light of the above, cannulation of the CSOs 250 can be achieved by analysis of an image of the instrument, including the radiopaque portion 30. The radiopaque portion 30 may include a selected geometry, including the geometries discussed above according to various embodiments, which may be analyzed to determine a position and orientation of the instrument 20. Additionally a probable location of the CSOs 250 can be based upon landmarks identified by the user. The triangulation of the probable location of the CSOs 250 can then be made and an icon 250i can be illustrated on the display device 232. Further analysis of the current location and orientation of the instrument, as discussed above, due to the image of the radiopaque portion 30, can then be used to provide suggested movements to achieve cannulation of the CSOs 250. Accordingly, an efficient cannulation of the CSOs 250 can be achieved by imaging the patient and/or the radiopaque portion 30 of the instrument 20. Secondary or alternative navigation members, such as an electromagnetic navigation tracking device and/or navigation system may not be required for directing the movement of the instrument 20 for cannulation of the CSOs 250.

The above described system and/or methods can assist the user in placing a catheter in the CSOs 250 to assist in obtaining image data, such as for a venogram, during a cardiac lead placement procedure. The image can be used as with the CardioGuide® imaging system for such a procedure. The system and method can also be used to assist a user to identify or select a location for positioning an instrument. The instrument may be a lead that can include a lead associated or used with an appropriate implantable medical device (IMD). The IMD can be selected devices, including a cardiac resynchronization system (CRT), stimulation devices, such as those used to stimulate anatomical or physiological responses (e.g. stimulation for muscle or nervous system responses), defibrillation, and other appropriate devices. Although an example herein is directed towards the CRT and related leads positioned in or near the coronary sinus, it is understood that any appropriate lead or IMD can be used.

A lead can be used to interconnect with an implantable medical case that can include a stimulation processor, power source, catheter, and other appropriate features. It is understood that the IMD can be implanted at any appropriate location relative to the patient. The associated lead is positioned at an appropriate location, such as relative to the coronary vessels 24. Cardiac leads may include the Attain™ cardiac simulation lead sold by Medtronic, Inc. and IMDs can include the VIVA XT® IMD or the Protecta® XT CRT-D IMD also sold by Medtronic, Inc. It is understood that the specific manufacturer of the lead and IMD is not necessary for the subject disclosure. As discussed further herein, a predetermined or acquired information or characteristic regarding various features, such as shape, size, lead cant and pushability of leads and/or implantation systems (e.g. catheters) can be acquired for any particular or desired lead and implantation system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. Moreover, specific exemplary embodiments are discussed with different features and this does not mean that they cannot be combined and/or eliminated in embodiments, unless specifically disclosed otherwise.

What is claimed is:

1. A method for moving an instrument to a selected location, comprising:
   determining an orientation of an imageable member based on an analysis of a region of interest in an image including the imageable member associated with the instrument;
   recalling a probable location of an ostium based upon a predetermined triangulated location of the ostium from selected landmarks in the image;
   displaying on a display device a target icon at the recalled probable location of the ostium;
   displaying on the display device the imageable member relative to the displayed target icon with the determined orientation of the imageable member;
   moving the instrument relative to the ostium based on the determined orientation of the imageable member and the displayed target icon;

receiving image data of the imageable member, wherein the image data may be used to generate the image for display; and executing instructions with a processor to perform the analysis of the region of interest in the image;

wherein executing instructions with a processor to perform the analysis of the region of interest in the image includes:

determining a center longitudinal line along a distal portion of the imageable member;

determining a first line extending substantially parallel to and on a first side of the center longitudinal line;

determining a second line extending substantially parallel to and on a second side of the center longitudinal line;

determining a first period length of high contrast portions intersecting the first line along its length; and determining a second period length of high contrast portions intersecting the second line along its length;

wherein the orientation of the imageable member is determined by evaluating at least one of the first period length or the second period length relative to a recalled manufacturer period length, an assumed period length, a maximum period length, or a calculation of an arc cosine within the region of interest.

2. A method for moving an instrument to a selected location, comprising:

analyzing a region of interest in an image to determine an orientation of an imageable member, wherein the image is a single image including the imageable member associated with the instrument, wherein the imageable member is a helical member wrapped around a longitudinal axis of the elongated member;

recalling a probable location of a target in the single image based upon a predetermined triangulated location of the target from selected landmarks in the single image;

displaying on a display device a target icon at the recalled probable location of the target on the single image;

displaying on the display device the helical member relative to the displayed target icon with the determined orientation of the imageable member; and determining the region of interest in the single image based upon movement of the helical member between a prior image and the single image;

wherein analyzing the region of interest in the single image to determine the orientation of the imageable member includes:

determining a center longitudinal line along a distal portion of the helical member;

determining a first line extending substantially parallel to and on a first side of the center longitudinal line;

determining a second line extending substantially parallel to and on a second side of the center longitudinal line;

determining a first period of high contrast portions intersecting the first line along its length;

determining a second period of high contrast portions intersecting the second line along its length; and evaluating the first period and the second period to determine the orientation of the imageable member;

wherein the instrument is configured to be moved within a volume relative to the target with the helical member wrapped around the instrument.

3. The method of claim 2, wherein analyzing the region of interest in the single image includes:

determining a period length of a coil portion of the helical member to determine an angle of the helical member, wherein the angle of the helical member is between a first portion and a second portion of the helical member;

analyzing a shape of the helical member in the single image to determine a direction of the helical member relative to the plane of the single image; and combine the determined angle and the determined direction to determine the orientation of the helical member as a combination of the determined angle and the determined direction.

4. The method of claim 2, wherein displaying on the display device the helical member includes displaying on the display device the imageable member as at least as one of a "n" shape or a "u" shape.

5. The method of claim 4, wherein analyzing the region of interest in the single image to determine the orientation of the imageable member further includes includes determining whether the imageable member is imaged as a "n" shape or a "u" shape.

6. The method of claim 2, further comprising:

determining a movement of the instrument relative to an ostium based on the determined orientation of the imageable member and the displayed target icon.

7. The method of claim 2, further comprising:

configuring the instrument to be moved in a determined movement relative to an ostium based on the determined orientation of the imageable member and the displayed target icon.

8. The method of claim 2, further comprising:

receiving the selected landmarks as at least a first landmark location and a second landmark location.

9. The method of claim 8, wherein receiving the selected landmarks includes receiving a manual input from a user.

10. The method of claim 2, further comprising:

determining the region of interest in the image by identifying a moving object in a plurality of images including the single image.

11. The method of claim 10, further comprising:

selecting at least a portion of the identified moving object as the region of interest.

12. The method of claim 2, further comprising:

displaying an imageable member icon representative of a first determined orientation of the imageable member at a first time relative to a displayed current determined orientation of the imageable member at a second time that is after the first time.

13. The method of claim 2, further comprising:

receiving image data of the imageable member; and wherein the received image data may be used to generate the image.

14. The method of claim 2, wherein determining the region of interest in the single image based upon movement of the helical member between the prior image and the single image comprises analyzing radiopaque properties of the helical member in the region of interest.

15. The method of claim 14, further comprising:

recalling from a memory system the radiopaque properties.

16. A method for moving an instrument to a selected location, comprising:

determining an orientation of an imageable member based on an analysis of a region of interest in an image including the imageable member associated with the instrument, wherein the image is a single image:

recalling a probable location of an ostium based upon a predetermined triangulated location of the ostium from selected landmarks in the image;

displaying on a display device a target icon at the recalled probable location of the ostium;

displaying on the display device the imageable member relative to the displayed target icon with the determined orientation of the imageable member at least as one of a "n" shape or a "u" shape for viewing by a user; and wherein the instrument is configured to be moved relative to the ostium;

wherein the imageable member is a helix coil;

wherein determining the orientation of the helix coil is based on the analysis of the region of interest in the image including the helix coil including:

determining a period length of helix coil to determine an angle of the helix coil, wherein the angle of the helix coil is between a first portion and a second portion of the helix coil;

analyzing a shape of the helix coil in the image to determine a direction of the helix coil relative to a plane of the image; and combining the determined angle and the determined direction to determine the orientation of the helix coil as a combination of the determined angle and the determined direction.

17. A method for moving an instrument to a selected location, comprising:

determining an orientation of an imageable member based on an analysis of a region of interest in an image including the imageable member associated with the instrument, wherein the image is a single image:

recalling a probable location of an ostium based upon a predetermined triangulated location of the ostium from selected landmarks in the image, displaying on a display device a target icon at the recalled probable location of the ostium;

displaying on the display device the imageable member relative to the displayed target icon with the determined orientation of the imageable member at least as one of a "n" shape or a "u" shape for viewing by a user; and providing the imageable member as a helix coil;

wherein the instrument is configured to be moved by the user relative to the ostium;

wherein determining the orientation of the imageable member includes:

determining a center longitudinal line along a distal portion of the helix coil;

determining at least one of a first line extending substantially parallel to and on a first side of the center longitudinal line or a second line extending substantially parallel to and on a second side of the center longitudinal line;

determining at least one of a first period length of high contrast portions of the helix coil intersecting the first line along its length or determining a second period length of high contrast portions of the helix coil intersecting the second line along its length; and calculating an angle of the helix coil based on the determined first period length or the second period length for determining the orientation of the imageable marker.

18. A method for moving an instrument to a selected location, comprising:

determining an orientation of an imageable member based on an analysis of a region of interest in an image including the imageable member associated with the instrument, wherein the image is a single image:

recalling a probable location of an ostium based upon a predetermined triangulated location of the ostium from selected landmarks in the image;

displaying on a display device a target icon at the recalled probable location of the ostium;

displaying on the display device the imageable member relative to the displayed target icon with the determined orientation of the imageable member at least as one of a "n" shape or a "u" shape for viewing by a user; and wherein the instrument is configured to be moved by the user relative to the ostium;

wherein determining the orientation of the imageable member based on the analysis of the region of interest in the image includes determining whether the imageable member is imaged as a "n" shape or a "u" shape.

19. The method of claim 18, further comprising providing the imageable member as a helical member.

* * * * *